United States Patent
Ariyoshi et al.

(10) Patent No.: US 9,317,658 B2
(45) Date of Patent: Apr. 19, 2016

(54) DATA MANAGEMENT COMPUTER, SAMPLE ANALYZING SYSTEM, AND COMPUTER PROGRAM

(75) Inventors: Shunsuke Ariyoshi, Kobe (JP); Shunsuke Yao, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 746 days.

(21) Appl. No.: 13/455,923

(22) Filed: Apr. 25, 2012

(65) Prior Publication Data

US 2012/0272755 A1     Nov. 1, 2012

(30) Foreign Application Priority Data

Apr. 28, 2011    (JP) ................................ 2011-100526

(51) Int. Cl.
| | |
|---|---|
| *G01N 35/00* | (2006.01) |
| *G06F 19/00* | (2011.01) |
| *G01N 35/04* | (2006.01) |

(52) U.S. Cl.
CPC ...... *G06F 19/3406* (2013.01); *G01N 35/00722* (2013.01); *G06F 19/366* (2013.01); *G01N 2035/0415* (2013.01)

(58) Field of Classification Search
None
See application file for complete search history.

(56) References Cited

U.S. PATENT DOCUMENTS

| | | |
|---|---|---|
| 2007/0179715 A1 | 8/2007 | Ariyoshi |
| 2009/0259408 A1* | 10/2009 | Mishima et al. ................ 702/19 |
| 2010/0105142 A1 | 4/2010 | Fukuma et al. |
| 2010/0112703 A1 | 5/2010 | Tanaka |
| 2010/0248374 A1 | 9/2010 | Kitagawa et al. |
| 2011/0077871 A1 | 3/2011 | Fukuma et al. |

FOREIGN PATENT DOCUMENTS

| | | |
|---|---|---|
| CN | 101726611 A | 6/2010 |
| JP | H9-81646 | 3/1997 |
| JP | 2000-46835 | 2/2000 |
| JP | 2003-329690 | 11/2003 |
| JP | 2010-107383 | 5/2010 |
| JP | 2010-236952 | 10/2010 |
| JP | 2011-75378 | 4/2011 |

\* cited by examiner

*Primary Examiner* — Robert R Raevis
(74) *Attorney, Agent, or Firm* — Brinks Gilson & Lione

(57) ABSTRACT

A data management computer for a sample measuring apparatus is disclosed. The computer comprises a data storage, a display section; an input device; and a controller. The data storage stores results of measurements for a sample obtained by the sample measuring apparatus, the measurements including an initial measurement for a sample and a secondary measurement which is performed on the sample following the initial measurement. The controller is programmed to cause the display section to display a first result screen which shows a result of the initial measurement for a sample, receive a predefined operation by use of the input device while displaying the first result screen, and cause the display section to display, in a response to the predefined operation, a second result screen which shows a result of the secondary measurement for the sample.

26 Claims, 15 Drawing Sheets

FIG. 4

| | C1 | C2 | C3 | C4 | C5 | C6 | C7 | C8 | C9 | C10 | |
|---|---|---|---|---|---|---|---|---|---|---|---|
| | RESULT ID | RECEIVED DATE AND TIME | MEASUREMENT DATE AND TIME | PATIENT ID | SAMPLE ID | ORDER TYPE | ERROR INFORMATION | MEASUREMENT UNIT | WBC | RBC | ... |
| | X1001 | 2010/10/8 21:01:57 | 2010/10/8 21:16:30 | P837 | 440 | Initial | NO | XN-10000-1-R | 43.1 | 399 | |
| | X1002 | 2010/10/8 21:19:12 | 2010/10/8 21:30:45 | P31 | 441 | Initial | NO | XN-10000-1-L | 42.8 | 401 | |
| | X1003 | 2010/10/8 21:19:13 | 2010/10/8 21:30:52 | P1001 | 442 | Initial | YES | XN-10000-1-L | 46.1 | 396 | |
| | . | . | . | . | . | . | . | . | . | . | |
| | X1015 | 2010/10/8 21:19:13 | 2010/10/8 21:31:54 | P1001 | 442 | Initial/Repeat | NO | | 46.2 | 398 | |
| | X1022 | 2010/10/8 21:19:13 | 2010/10/8 21:33:15 | P1001 | 442 | Reflex | YES | XN-10000-1-L | 46.1 | 395 | |
| | X1030 | 2010/10/8 21:19:13 | 2010/10/8 21:34:50 | P1001 | 442 | Reflex/Repeat | NO | XN-10000-1-L | 45.9 | 400 | |
| | . | . | . | . | . | . | . | . | . | . | |
| | X4003 | 2011/4/5 9:02:10 | 2011/10/5 9:30:44 | P31 | 11 | Initial | NO | XN-10000-1-L | 45.0 | 399 | |
| | . | . | . | . | . | . | . | . | . | . | |
| | X9600 | 2011/11/1 18:35:40 | 2011/11/1 20:30:22 | P31 | 1033 | Initial | NO | XN-10000-1-L | 46.1 | 396 | |

| SAMPLE ID (C11) | ORDER TYPE (C12) | MEASUREMENT DISCRETE (C13) |
|---|---|---|
| 440 | Initial | CBC+DIFF |
| 441 | Initial | CBC+DIFF |
| 442 | Initial | CBC+DIFF |
| . | . | . |
| . | . | . |
| . | . | . |
| 442 | Initial/Repeat | CBC+DIFF |
| . | . | . |
| . | . | . |
| 442 | Reflex | CBC+DIFF+RET |
| . | . | . |
| 442 | Reflex/Repeat | CBC+DIFF+RET |

M101 → row 1; M102 → Initial/Repeat row; M103 → Reflex row; M104 → Reflex/Repeat row

DATA MANAGEMENT COMPUTER, SAMPLE ANALYZING SYSTEM, AND COMPUTER PROGRAM

RELATED APPLICATIONS

This application claims priority under 35 U.S.C. §119 to Japanese Patent Application No. 2011-100526 filed on Apr. 28, 2011, the entire content of which is hereby incorporated by reference.

BACKGROUND OF THE INVENTION

1. Field of the Invention

The present invention relates to a data management computer including a display section for displaying measurement results obtained by measuring a sample. The present invention also relates to an analyzing system including a sample measuring apparatus for measuring a sample, and the data management computer. The present invention further relates to a computer program for operating a computer for displaying the measurement results obtained by measuring a sample.

2. Description of the Related Art

A sample analyzer for displaying the measurement results obtained by measuring a sample is conventionally known.

U.S. Patent application publication No. 2007-0179715 discloses an analyzer including a measuring apparatus for measuring a sample and generating particle measurement data, and a computer for analyzing the particle measurement data received from the measuring apparatus, and generating detailed information including numerical value data, particle size distribution diagram, and scattergram. The computer includes a display. As shown in FIG. 3 of U.S. Patent application publication No. 2007-0179715, the computer can display a list of measurement results for a plurality of samples. The operator can select one measurement result from the list. The operator can see the detailed information of the selected measurement result, such as the particle size distribution and the scattergram, as shown in FIG. 1 and FIG. 2 of U.S. Patent application publication No. 2007-0179715 by selecting one from the list.

When users such as clinical laboratory technicians refer the measurement results, they sometimes refer one measurement result as well as other measurement results related thereto. For instance, to determine whether a validation should be made on a measurement result of a re-test, the users sometimes refer a measurement result of an initial test of the same sample. Or, in other case, to determine whether a validation should be made on a measurement result of a sample, the users sometimes refer a measurement result of the past sample obtained from the same patient.

In the prior art, if the users desire to see detailed information of related measurement result while referring detailed information of one measurement result, the users have to once close the detailed information screen, open a list, search a related measurement result therefrom, and then open the detailed information screen of the searched measurement result.

SUMMARY OF THE INVENTION

A first aspect of the present invention is a data management computer for a sample measuring apparatus comprising: a data storage for storing results of measurements for a sample obtained by the sample measuring apparatus, the measurements including an initial measurement for a sample and a secondary measurement which is performed on the sample following the initial measurement; a display section; an input device; and a controller programmed to: cause the display section to display a first result screen which shows a result of the initial measurement for a sample; receive a predefined operation by use of the input device while displaying the first result screen; and cause the display section to display, in a response to the predefined operation, a second result screen which shows a result of the secondary measurement for the sample.

A second aspect of the present invention is a sample analyzing system comprising: one or more sample measuring apparatuses for measuring a sample; a data storage for storing results of measurements for a sample obtained by the sample measuring apparatus, the measurements including an initial measurement for a sample and a secondary measurement which is performed on the sample following the initial measurement; a data management computer communicably connected to the data storage, wherein the data management computer includes a display section; an input device; and a controller which is programmed to: cause the display section to display a first result screen which shows a result of the initial measurement for a sample; receive a predefined operation by use of the input device while displaying the first result screen; and cause the display section to display, in a response to the predefined operation, a second result screen which shows a result of the secondary measurement for the sample.

A third aspect of the present invention is a computer program product for causing a computer including an input device and a display section to function as a data management computer for a sample measuring apparatus, the computer program product comprising: a computer readable medium; and an instruction stored in the computer readable medium, wherein the instruction comprising: causing the display section to display a first result screen which shows a result of an initial measurement for a sample; receiving a predefined operation by use of an input device while displaying the first result screen; and causing the display section to display, in a response to the predefined operation, a second result screen which shows a result of a secondary measurement which is performed on the sample following the initial measurement.

A fourth aspect of the present invention is a data management computer for a sample measuring apparatus comprising: a data storage for storing results of measurements for samples obtained by the sample measuring apparatus, the measurement result including a plurality of results for a plurality of samples collected from a same patient; a display section; an input device; and a controller programmed to: cause the display section to display a first result screen which shows a result of measurement on a first sample collected from a patient; receive a predefined operation by use of the input device while displaying the first result screen; and cause the display section to display, in response to the predefined operation, a second result screen which shows a result of measurement on a second sample collected from the patient.

BRIEF DESCRIPTION OF THE DRAWINGS

FIG. 4 is a view schematically showing a data structure of a measurement result list according to the embodiment;

FIG. 6 is a view schematically showing a data structure of an order list according to the embodiment;

DETAILED DESCRIPTION OF THE PREFERRED EMBODIMENTS

[Configuration of Sample Analyzer]

Figure 1:
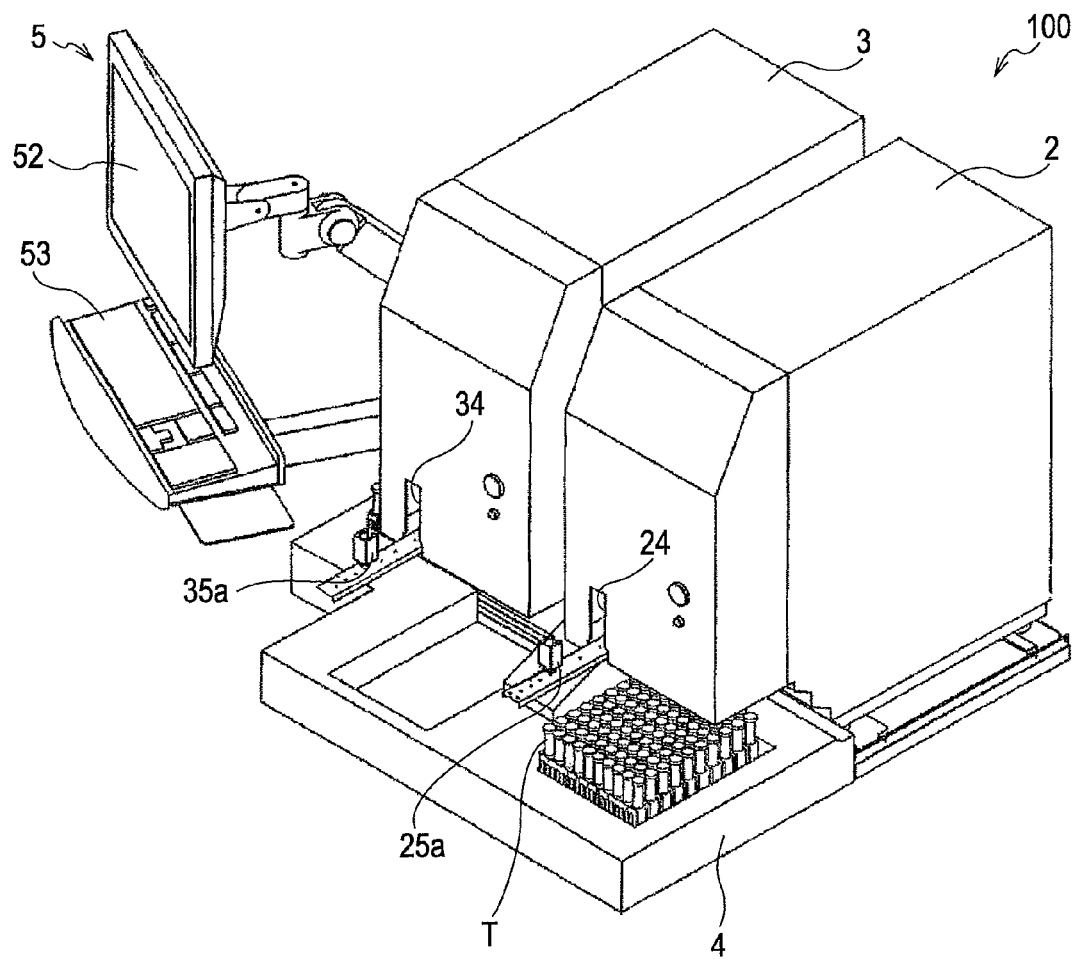
FIG. 1 is a perspective view showing an overall configuration of a sample analyzer according to an embodiment.

FIG. 1 is a perspective view of a sample analyzer according to the present embodiment. A sample analyzer 100 according to the present embodiment is a multi-item blood cell analyzer for measuring a blood sample contained in a sample container T including a vacuum blood collecting tube, classifying the blood cells contained in the blood sample to white blood cells, red blood cells, blood platelets, and the like, and counting each blood cell.

The sample analyzer 100 shown in FIG. 1 includes two measurement units 2, 3, a sample transport unit 4 arranged on the front surface side of the measurement units 2, 3, and an information processing unit 5 for controlling the measurement units 2, 3 and the sample transport unit 4.

[Configuration of Measurement Unit]

Figure 2:
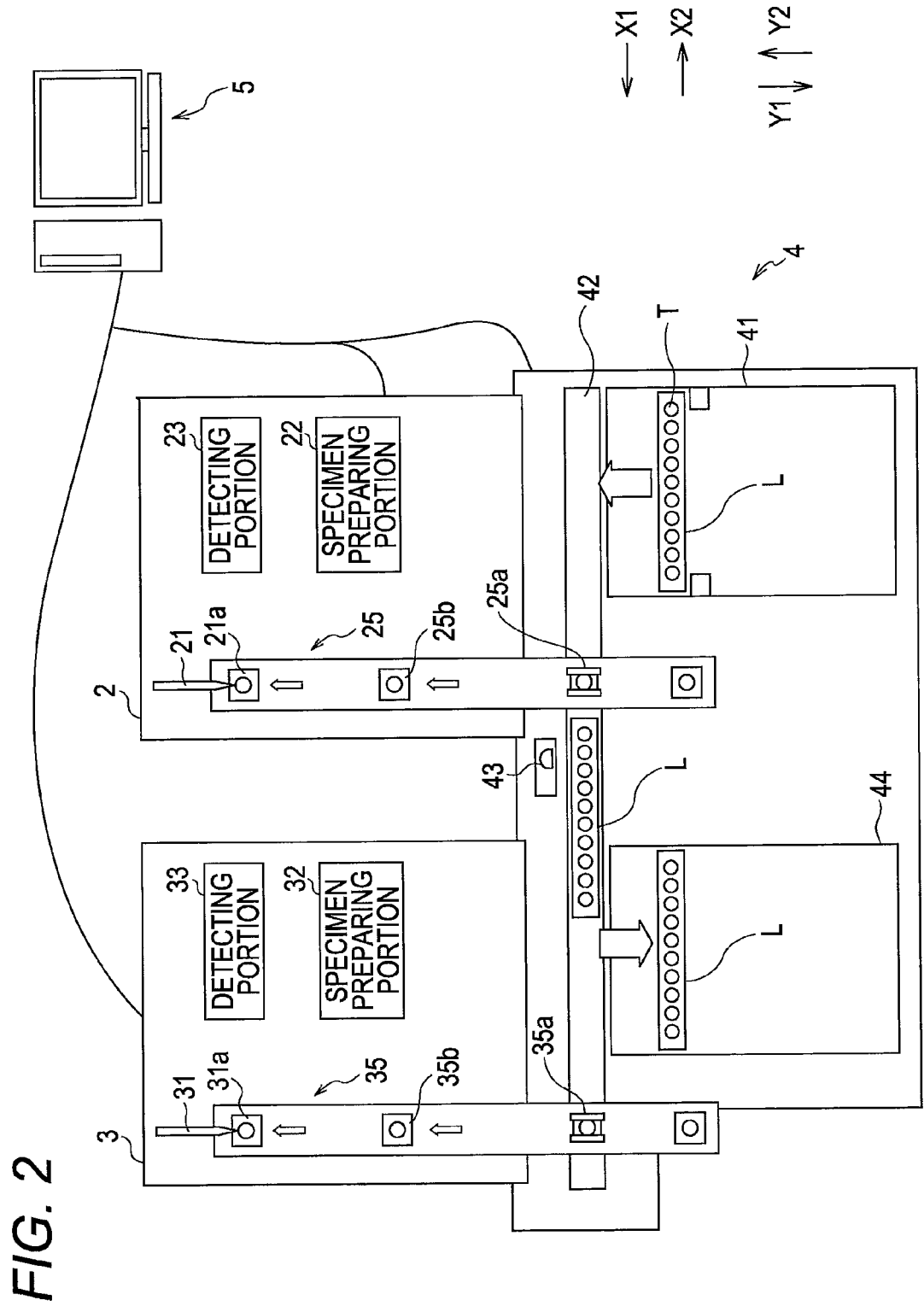
FIG. 2 is a plan view showing a configuration of when the interior of the sample analyzer according to the embodiment is seen from an upper side.

FIG. 2 is a schematic view showing a configuration of the sample analyzer 100 shown in FIG. 1. The measurement unit 2 is arranged on an upstream side (X2 direction side) in the transporting direction of the sample of the sample transport unit 4, and the measurement unit 3 is arranged on a downstream side (X1 direction side) in the transporting direction.

As shown in FIG. 2, the measurement unit 2 includes a sample aspirating portion 21 for aspirating the blood sample from the sample container (blood collecting tube) T, a specimen preparing portion 22 for preparing a measurement specimen used in the measurement of the blood component such as the blood cell from the blood aspirated by the sample aspirating portion 21, and a detecting portion 23 for detecting the blood cell from the measurement specimen prepared by the specimen preparing portion 22.

The measurement unit 2 further includes a take-in port 24 (see FIG. 1) for taking in the sample container T accommodated in a sample rack L transported by the sample transport unit 4 into the measurement unit 2, and a sample container transporting portion 25 for taking in the sample container T from the sample rack L into the measurement unit 2, and transporting the sample container T up to an aspirating position 21a by the sample aspirating portion 21.

The sample container transporting portion 25 includes a hand part 25a capable of gripping the sample container T, and a sample container setting part 25b with a hole for receiving the sample container T. The hand part 25a is movable in an up and down direction and in a front and back direction (Y1 direction and Y2 direction), and can grip the sample container T accommodated in the sample rack L, take out the sample container T from the sample rack L, and set the same in the sample container setting part 25a. When the sample container setting part 25b is moved backward (Y2 direction), the sample container T is taken into the measurement unit 2, and the sample container T is transported up to the aspirating position 21a.

[Configuration of Sample Transport Unit]

The sample transport unit 4 includes a pre-measurement rack holding portion 41 in which the sample rack L holding the sample container before the measurement is arranged, a transport path 42 for transporting the sample rack L to the left and right (X1 direction and X2 direction), and a post-measurement rack holding portion 44 in which the sample rack L holding the sample container after the measurement is arranged. The sample transport unit 4 further includes a barcode reader 43 for reading a barcode label attached to the sample container T held in the sample rack transported by the transport path 42. The barcode label of the sample container T stores sample identification information (hereinafter referred to as sample ID) for identifying the blood sample contained in the sample container.

[Configuration of Information Processing Unit]

A configuration of the information processing unit 5 will now be described. The information processing unit 5 analyzes the measurement data output from the measurement units 2, 3, creates a particle size distribution (histogram) of red blood cells and a two-dimensional distribution diagram (scattergram) of white blood cells, and counts the number of blood cells of each sub-class (NEUT, LYMPH, EO, BASO, and MONO) of the white blood cells to generate the measurement result of the sample and display such measurement result.

Figure 3:
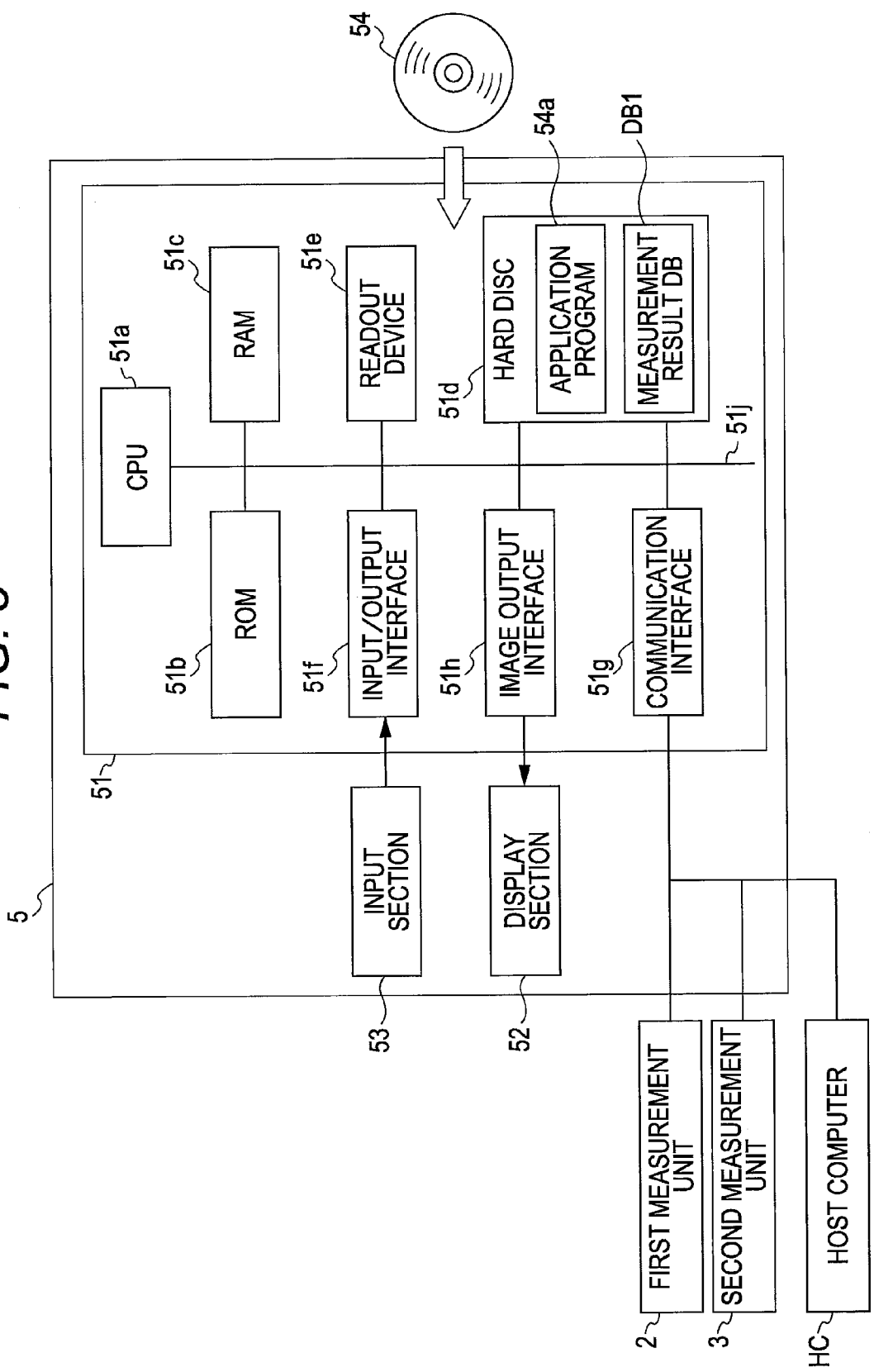
FIG. 3 is a block diagram showing a configuration of an information processing unit according to the embodiment.

The information processing unit 5 is configured by a computer. FIG. 3 is a block diagram showing a configuration of the information processing unit 5. As shown in FIG. 3, the information processing unit 5 includes a computer main body 51, a display section 52, and an input section 53. The computer main body 51 includes a CPU 51a, a ROM 51b, a RAM 51c, a hard disc 51d, a readout device 51e, an input/output interface 51f, a communication interface 51g, and an image output interface 51h. The CPU 51a, the ROM 51b, the RAM 51c, the hard disc 51d, the read-out device 51e, the input/output interface 51f, the communication interface 51g, and the image output interface 51h are connected by a bus 51j.

The readout device 51e can read out a computer program 54a for causing the computer to function as the information processing unit 5 from a portable recording medium 54, and install the computer program 54a in the hard disc 51d.

The input/output interface 51f is configured by serial interface such as USB, IEEE1394, RS-232C; parallel interface such as SCSI, IDE, IEEE1284; analog interface such as D/A converter, A/D converter, and the like. The input/output interface 51f is connected to the input section 53 including a keyboard, mouse, and a touch panel, so that the user can use the input section 53 to input data to the computer 5a or operate the screen of the computer 5a. The input/output interface 51f is also connected to the measurement units 2, 3 and the sample transport unit 4 through a communication cable. The information processing unit 5 thus can control each of the measurement units 2, 3 and the sample transport unit 4.

The hard disc 51d includes a measurement result database DB1 for storing a plurality of measurement results for a plurality of samples.

[Structure of Measurement Result Database]

A data structure of the measurement result database DB1 will be described with reference to FIG. 4. FIG. 4 is a schematic view showing a data structure of a measurement result list L100 stored in the measurement result database DB1 of the hard disc 51d.

As shown in FIG. 4, the measurement result list L100 includes a result ID column C1, a received date and time column C2, a measurement date and time column C3, a patient ID column C4, a sample ID column C5, an order type column C6, an error information column C7, a unit information column C8, and numerical value data columns C9, C10, . . . .

The result ID column C1 stores a result ID, which is an identification number for identifying each row (also referred to as record) stored in the measurement result list L100. The result ID is newly assigned every time a record is added to the measurement result list L100.

The received date and time column C2 stores a date and time at which the sample analyzer 100 received the sample. The date and time at which the sample is received is the date and time at which the barcode label of the sample container is read by the barcode reader 43.

The measurement date and time column C3 stores a date and time at which the sample is measured. The date and time at which the sample is measured is the date and time at which the measurement data output from the sample measurement units 2, 3 is input to the information processing unit 5 through the communication interface 51g.

The patient ID column C4 stores a patient ID as identification information for identifying the patient from whom the sample is collected. The patient ID is assigned for every patient to identify each patient.

The sample ID column C5 stores a sample ID for identifying the sample contained in the sample container. The sample ID is assigned for every sample to identify each sample, where the information is incorporated in the barcode label attached to the sample container. The sample ID obtained by reading the barcode label with the barcode reader 43 is stored in the column C5 by the information processing unit 5.

The order type column C6 stores a type of measurement carried out to generate the measurement result. In the present embodiment, the type of measurement includes the following six types, "Initial", "Initial/Repeat", "Rerun", "Rerun/Repeat", "Reflex", and "Reflex/Repeat". One of them is stored in the order type column C6.

In the present specification, "Initial" is referred to as initial measurement (or initial test) which is initially performed on a sample. Also, in the present specification, "re-measurement" (or re-test) means a measurement which is performed on the same sample with the initial test, following the initial test. That is, the initial test includes an aspiration of a quantity of sample from a sample container and a measurement on the aspirated sample. The re-test includes an aspiration of a quantity of sample from the same sample container and a measurement on it.

"Initial" is the initial measurement. The initial measurement is the measurement carried out first when the sample analyzer 100 receives the sample.

"Initial/Repeat" is the measurement executed when error occurs in "Initial". The error occurs when analysis cannot be executed since there is too much noise in the measurement data received from the measurement unit 2, or when the sample cannot be aspirated although the measurement unit 2 attempts to aspirate the sample, due to lack of sample amount. In the measurement by such type, the measurement is carried out for the measurement item same as in the initial measurement.

"Rerun" is the measurement executed when the numerical value data of the measurement result by "Initial" or "Initial/Repeat" is within an abnormal numerical value range. In the measurement by such type, the measurement is carried out for the measurement item same as in "Initial".

"Rerun/Repeat" is the measurement executed when error occurs in "Rerun". In the measurement by such type, the measurement is carried out for the measurement item same as in "Rerun".

"Reflex" is the measurement executed when the numerical value data of the measurement result by "Initial" or "Initial/Repeat" is within a numerical value range defined in advance. In the measurement by such type, an additional measurement item is measured in addition to the measurement item of "Initial". For instance, if the measurement item of "Initial" is "CBC+DIFF", "RET" is added and "CBC+DIFF+RET" is measured.

"Reflex/Repeat" is the measurement executed when error occurs in "Reflex". In the measurement by such type, the measurement is carried out for the measurement item same as in "Reflex".

The error information column C7 stores presence/absence of error for the measurement carried out to generate the measurement result.

The unit information column C8 stores an identification number of the measurement unit that carried out the measurement for generating the measurement result. In the present embodiment, the identification number of the measurement unit 2 is defined as "XN-10000-1-R", and the identification number of the measurement unit 3 is defined as "XN-10000-1-L".

The numerical value data columns C9, C10 store numerical value data of the measurement result. In FIG. 4, the numerical value data of the number of white blood cells (WBC) is stored in the column C9, and the numerical value data of the number of red blood cells (RBC) is stored in C10. In FIG. 4, only C9 and C10 are illustrated, and the illustrations of subsequent columns are omitted.

[Measurement Operation]

The processing operation in units of a sample rack of the sample analyzer 100 will now be described. The operation starts when the user sets the sample rack in the pre-measurement rack holding portion 41, and instructs the start of processing through the input section 53 of the information processing unit 5.

When the operation is started, the sample transport unit 4 first transports the sample. Specifically, the sample transport unit 4 moves the sample rack L backward (Y2 direction) from the pre-measurement rack holding portion 41 towards the transport path 42 when receiving the instruction to start the process. When receiving the sample rack L, the transport path 42 moves the sample rack L towards the downstream (X1 direction) in the transporting direction, and transports the sample rack so that a plurality of sample containers T held in the sample rack L is positioned in front of the barcode reader 43 one by one. The barcode reader 43 reads the barcode of each sample container T.

After the barcode label of all the sample containers T held in the sample rack L is read, each sample container T is transported to either the measurement unit 2 or the measurement unit 3. Specifically, the sample container T held at the odd number from the X1 direction of the sample rack L is transported to the measurement unit 2. The sample container T held at the even number from the X1 direction of the sample rack L is transported to the measurement unit 3. The measurement units 2, 3 also carry out the first measurement (also referred to as initial test) on the sample contained in the transported sample container T.

When the measurement is carried out on the sample, whether re-measurement is necessary is determined for the relevant sample. If determined that the re-measurement is necessary, the sample container T containing such sample is transported to either the measurement unit 2 or the measurement unit 3, and re-measurement is carried out. If determined that the re-measurement is not necessary for all the sample containers T held in the sample rack L, the transport path 42 transports the sample rack L to the back side (Y2 direction side) of the post-measurement rack holding portion 44. The sample rack L is moved forward (Y1 direction side), and fed to the post-measurement rack holding portion 44.

[Sample Measuring Operation]

Figure 5:
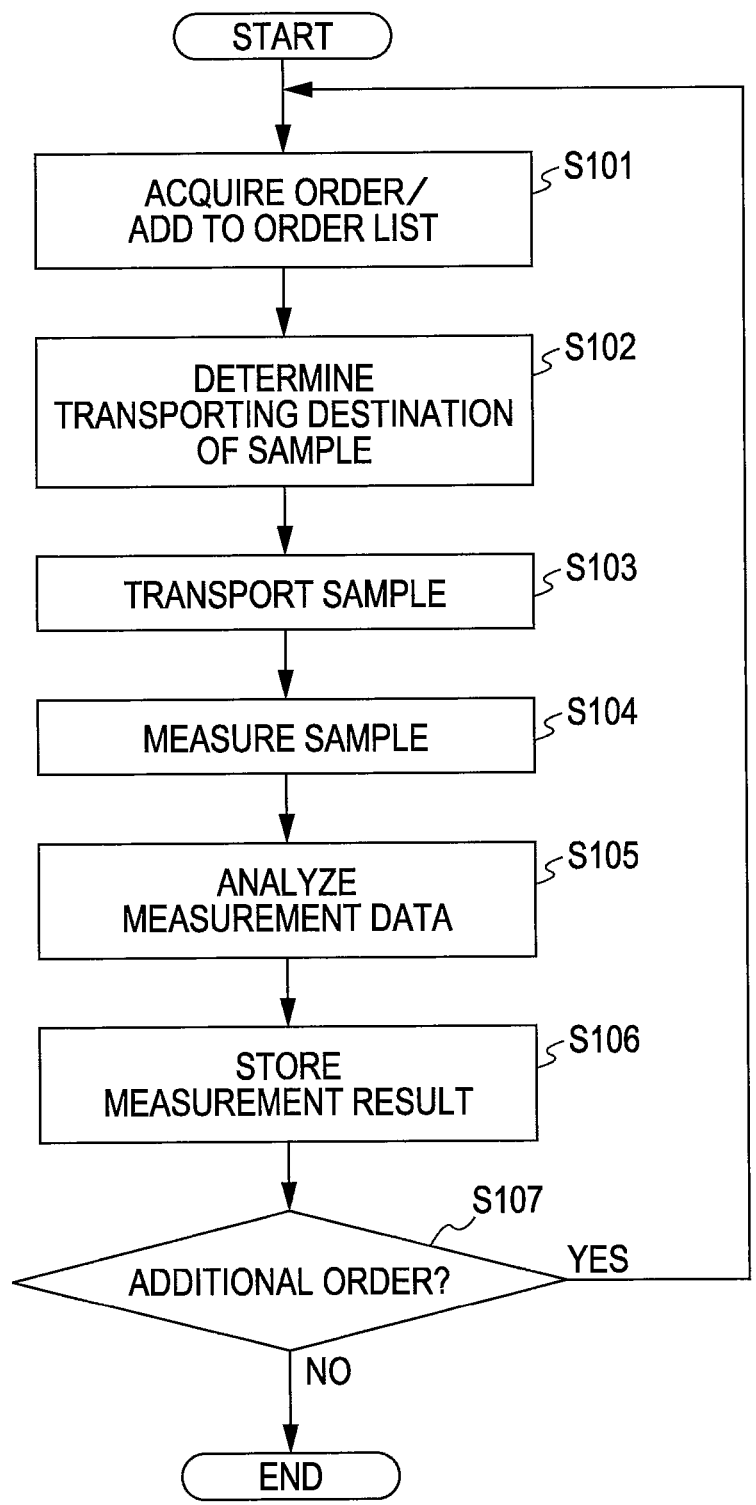
FIG. 5 is a flowchart showing the operation of the sample analyzer according to the embodiment.

The processing operation in units of a sample container will be described below using a flowchart. FIG. 5 is a flowchart showing the operation of the sample analyzer 100.

After the barcode label attached to the sample container T is read by the barcode reader 43, the read result is transmitted to the information processing unit 5, so that the information processing unit 5 acquires an order based on the received read result and adds the same to an order list (step S101).

Specifically, the information processing unit 5 transmits a sample ID contained in the read result to the host computer HC and inquires the host computer HC on the measurement order when receiving the read result. The patient ID and the measurement order are registered in advance in the host computer HC in association with the sample ID. The host computer HC transmits the registered measurement order and the patient ID associated with the received sample ID to the information processing unit 5. The information processing unit 5 registers a new order in the order list when receiving the measurement order.

FIG. 6 is a view schematically showing a data structure of an order list. As shown in FIG. 6, an order list L200 includes a sample ID column C11 storing a sample ID, an order type column C12 storing an order type, and a measurement discrete column C13 storing a measurement discrete item.

When receiving the measurement order from the host computer HC, the information processing unit 5 adds a new order to the bottom line of the order list. The sample ID read from the sample container T is input to the column C11 of the new order. The measurement discrete item contained in the received measurement order is input to the column C13. The order type is input to the column C12. "Initial" is input to the column C12 in the case of a new order, and an order type set according to the re-test determination rule (see FIG. 7), to be described later, is input in the case of an additional order. The new order is an order added to the list based on the measurement order received from the host computer HC. The additional order is an order automatically generated by the information processing unit 5 when the information processing unit 5 determines as according with the re-test determination rule (see FIG. 7), to be described later, as a result of executing the measurement based on the measurement order registered in the order list L200.

Returning back to FIG. 5, the information processing unit 5 determines a transporting destination of the sample container T in which the barcode is read (step S102). Specifically, the information processing unit 5 determines whether to transport the sample container T to the first measurement unit 2 or the second measurement unit 3. A case in which the transporting destination of the sample container T is determined as the first measurement unit 2 will be illustratively described below.

The sample transport unit 4 transports the sample container T to the measurement unit determined as the transporting destination (step S103). Specifically, the sample transport unit 4 transports the sample container T to a position immediately below the hand part 25a of the first measurement unit 2.

The first measurement unit 2 measures the sample contained in the transported sample container T (step S104). Specifically, the measurement unit 2 grips the sample container T with the hand part 25a and takes out the sample rack L from the sample container T. The hand part 25a sets the sample container T in the sample container setting part 25b of the sample transporting portion 25. The sample container transporting portion 25 is then moved backward, and the sample container T is taken into the measurement unit 2. The sample container T is transported to the aspirating position 21a by the aspirating portion 21. The aspirating portion 21 is pierced into the sample container T transported to the aspirating position 21a, and aspirates the blood sample contained in the sample container T. The aspirated blood sample is sent to the specimen preparing portion 22. The specimen preparing portion 22 prepares a measurement specimen by mixing the supplied blood sample and a reagent. The prepared measurement specimen is supplied to the detecting portion 23. The detecting portion 23 electrically and optically measures the supplied measurement specimen, and generates measurement data including electrical signals. The measurement data is provided to the information processing unit 5.

The information processing unit 5 stores the provided measurement data in the hard disc 51d, and analyzes the measurement data to generate the measurement result (step S105). Specifically, the information processing unit 5 analyzes the measurement data to generate numerical value data such as number of red blood cells, number of white blood cells, and number of blood platelets, and creates a particle size distribution (histogram) of the red blood cells and the blood platelets as well as a two-dimensional distribution diagram (scattergram) two-dimensionally showing a distribution of subclasses of the white blood cells.

The information processing unit 5 stores the generated measurement result in the measurement result database DB1 (step S106). Specifically, the information processing unit 5 adds a new record to the bottom line of the measurement result list L100 of the measurement result database DB1. The date and time at which the barcode label of the sample container T is read by the barcode reader 43 is input to the received date and time column C2 of the row of the new record. The date and time at which the measurement data output from the sample measurement unit 2 is input to the information processing unit 5 via the communication interface 51g is input to the measurement date and time column C3. The patient ID provided from the host computer HC with the measurement order is input to the patient ID column C4. The sample ID obtained by reading the barcode label of the sample container T with the barcode reader 43 is input to the sample ID column C5. The order type input to the column C12 of the order list L200 is input to the order type column C6. "Yes" is input to the error information column C7 if error occurs, and "No" is input if error does not occur. "XN-10000-1-R", which is the identification number of the measurement unit 2 is input to the unit information column C8 in the above example. The numerical value data of the measurement result obtained in step S106 is input to the corresponding column in the numerical value data columns C9, C10. The histogram and the scattergram created in step S106 are stored in the hard disc 51d in association with the added new record.

The information processing unit 5 then determines whether or not to generate an additional order (step S107). This process will be described with reference to FIG. 7.

Figure 7:
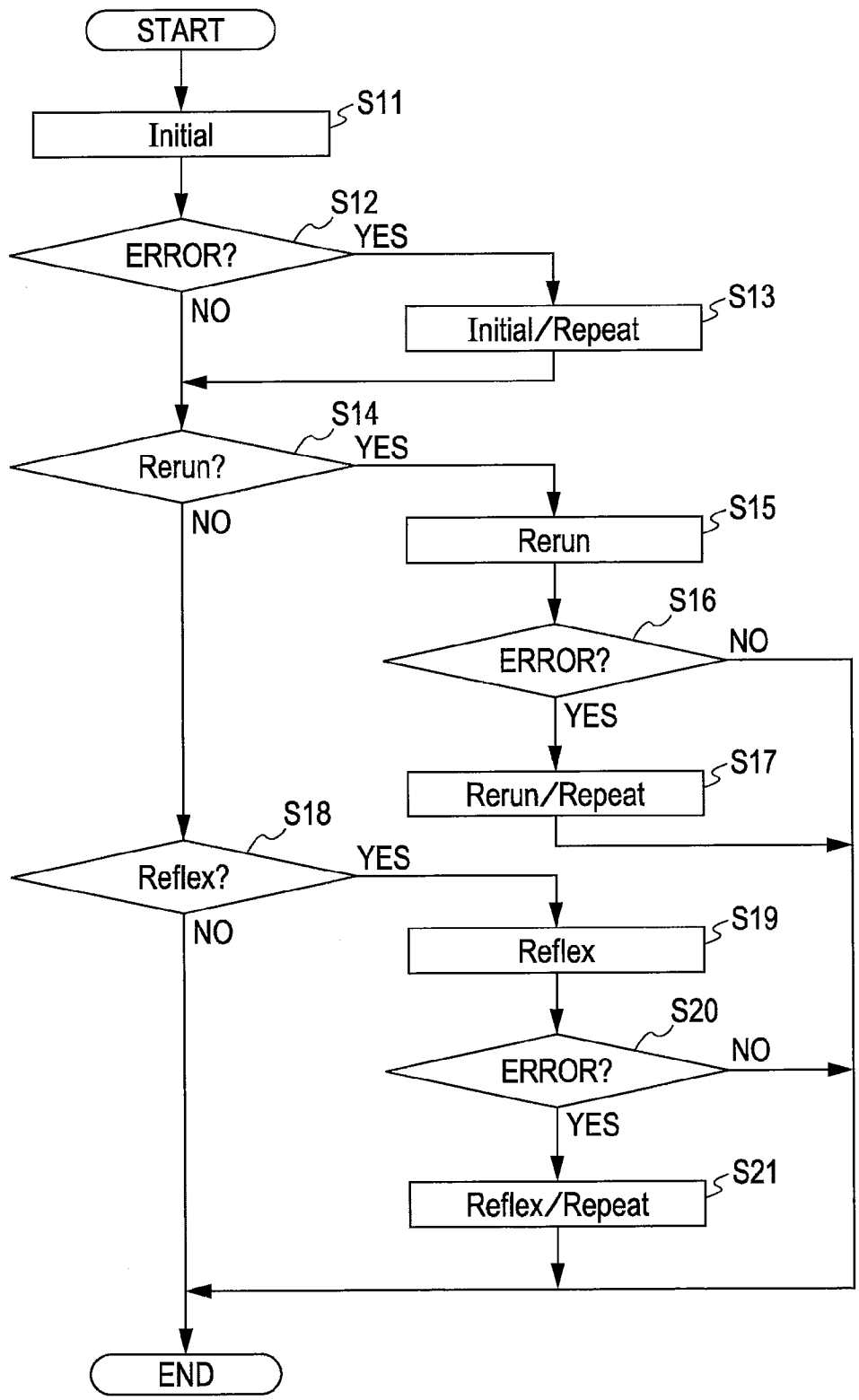
FIG. 7 is a flowchart showing a re-test determination rule in the sample analyzer according to the embodiment.

FIG. 7 is a flowchart showing a re-test determination rule for determining whether or not to generate the additional order. The information processing unit 5 automatically determines whether or not to generate the additional order, that is, whether or not re-test is necessary with reference to the re-test determination rule every time one measurement is completed.

When "Initial" is measured for a certain sample (step S11), the information processing unit 5 determines whether or not an error occurred in the measurement of "Initial" (step S12).

If determined that error occurred (step S12: Yes), the information processing unit 5 generates "Initial/Repeat" as the additional order (step S13).

As will be described in detail later, the generated additional order is added to the bottom line of the order list L200, and the re-measurement is automatically executed based on the additional order.

If determined that the error did not occur (step S12: No), the process proceeds to step S14.

The information processing unit 5 determines whether or not the condition to measure "Rerun" is satisfied as a result of the measurement of "Initial" or "Initial/Repeat" (step S14). In the present embodiment, the condition of "Rerun" is satisfied when the numerical value of one measurement item measured by "Initial" or "Initial/Repeat" is in an abnormal numerical value range set in advance. If determined that the condition of "Rerun" is not satisfied (step S14: No), the process proceeds to step S18. If determined that the condition of "Rerun" is satisfied (step S14: Yes), the information processing unit 5 generates "Rerun" as the additional order (step S15).

The information processing unit 5 determines whether or not an error occurred as a result of the measurement of "Rerun" (step S16). The determination on whether or not an error occurred is similar to step S12. If determined that error occurred, the information processing unit 5 generates "Rerun/Repeat" as the additional order (step S17). If determined that the error did not occur (step S16: No), the additional order is not generated, and a series of measurements on such sample is terminated.

In step S18, whether or not the result of "Initial" or "Initial/Repeat" accords with the condition to measure "Reflex" (step S18) is determined. In the present embodiment, the condition of "Reflex" is satisfied when the numerical value of one measurement item measured by "Initial" or "Initial/Repeat" is not in the abnormal numerical value range but in a numerical range set in advance. If determined that the condition of "Reflex" is not satisfied (step S18: No), the additional order is not generated, and a series of measurements on such sample is terminated. If determined that the condition of "Reflex" is satisfied (step S18: Yes), the information processing unit 5 generates "Reflex" as the additional order (step S19).

The information processing unit 5 determines whether or not an error occurred as a result of the measurement of "Reflex" (step S20). The determination on whether or not an error occurred is similar to step S12. If determined that error occurred, the information processing unit 5 generates "Reflex/Repeat" as the additional order (step S21). If determined that the error did not occur (step S20: No), the additional order is not generated, and a series of measurements on such sample is terminated.

Returning back to FIG. 5, the information processing unit 5 determines whether or not to generate an additional order with reference to the re-test determination rule in step S107.

If determined not to generate the additional order (step S107: No), a series of processes on the relevant sample is completed. If determined to generate the additional order (step S107: Yes), the process returns to step S101, and the information processing unit 5 adds the additional order at the bottom line of the order list L200. The adding process of the additional order to the order list L200 will be described with reference to FIG. 6.

With reference to FIG. 6, if "Initial/Repeat" is generated for the additional order as a result of measuring "Initial" for the sample of sample ID: 442 based on a new order of M101, sample ID: 442 same as "Initial" is input to the column C11 of the additional order M102, and "Initial/Repeat" is input to the column C12. "Initial/Repeat" is the order type for measuring the same measurement discrete item as "Initial", and thus "CBC+DIFF" same as the order M101 is input to the column C13.

If "Reflex" is generated for the additional order as a result of measuring "Initial/Repeat" for the sample of sample ID: 442 based on the additional order of M102, sample ID: 442 same as "Initial/Repeat" is input to the column C11, and "Reflex" is input to the order type. In "Reflex", the measurement discrete item measured immediately before for the relevant sample is added. Thus, "RET" is added to the measurement discrete item of "CBC+DIFF", and "CBC+DIFF+RET" is input to the column C13 of the additional order M103.

If "Reflex/Repeat" is generated for the additional order as a result of measuring "Reflex" for the sample of sample ID: 442 based on the additional order of M103, sample ID: 442 same as "Reflex" is input to the column C11 of the additional order M104, and "Reflex/Repeat" is input to column C12. "Reflex/Repeat" is the order type for measuring the same measurement discrete item as "Initial", and thus "CBC+DIFF+RET" same as the order M103 is input to the column C13.

Returning back to FIG. 5, when determining to generate the additional order (step S107: YES), the information processing unit 5 adds the additional order to the order list L200 (step S101), and again executes the processes of step S102 to step S106 based on the added order.

After the processes up to step S106 are finished for the additional order, the information processing unit 5 registers the measurement result by the additional order in the measurement result list L100 of the measurement result database DB1 (step S106).

The process of when registering the measurement result by the additional order in the measurement result database DB1 will be described with reference to FIG. 4. The information processing unit 5 adds the measurement result generated by the additional order as a new record to the bottom line of the measurement result list.

The process of when registering the measurement result generated by the additional order M102 (see FIG. 6) will be described here by way of example. The additional order M102 is an additional order of re-measurement based on the new order M101 (see FIG. 6), and thus the measurement result record (result ID: X1015) of the additional order M102 is created based on the measurement result record (result ID: X1003) of the new order M101. Specifically, the received date and time, the patient ID, and the sample ID same as the record (X1003) are input to the columns C2, C4, C5 of the record (X1015). The date and time at which the additional order M102 is measured is input to the column C3. The order type "Initial/Repeat" set in the additional order M102 is input to the column C6. The identification information of the measurement unit that carried out the measurement of the additional order is input to the column C8. The numerical value data obtained by the measurement of the additional order is input to the columns C9, C10.

The measurement of the sample is terminated by the processes described above. A plurality of measurement result records is accumulated in the measurement result database DB1 by performing the process over plural times.

[Measurement Result Displaying Process]

The process of displaying the measurement result stored in the measurement result database DB1 will now be described.

Figure 8:
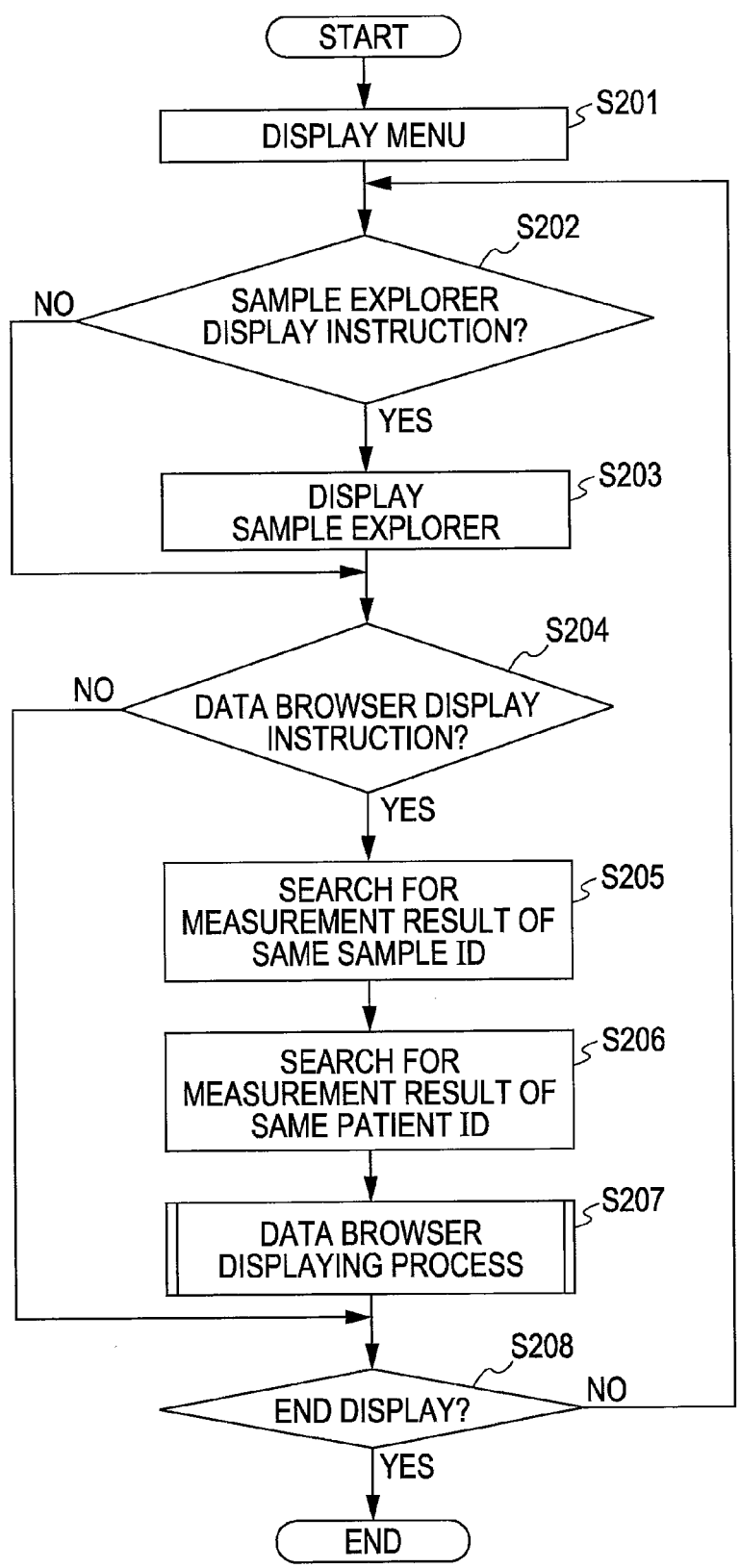
FIG. 8 is a flowchart showing a displaying process according to the embodiment.

FIG. 8 is a flowchart showing the displaying process. First, the information processing unit 5 displays a menu screen D1 shown in FIG. 10 on the display section 52 when the application program stored in the hard disc 51d is started (step S201).

Figure 10:
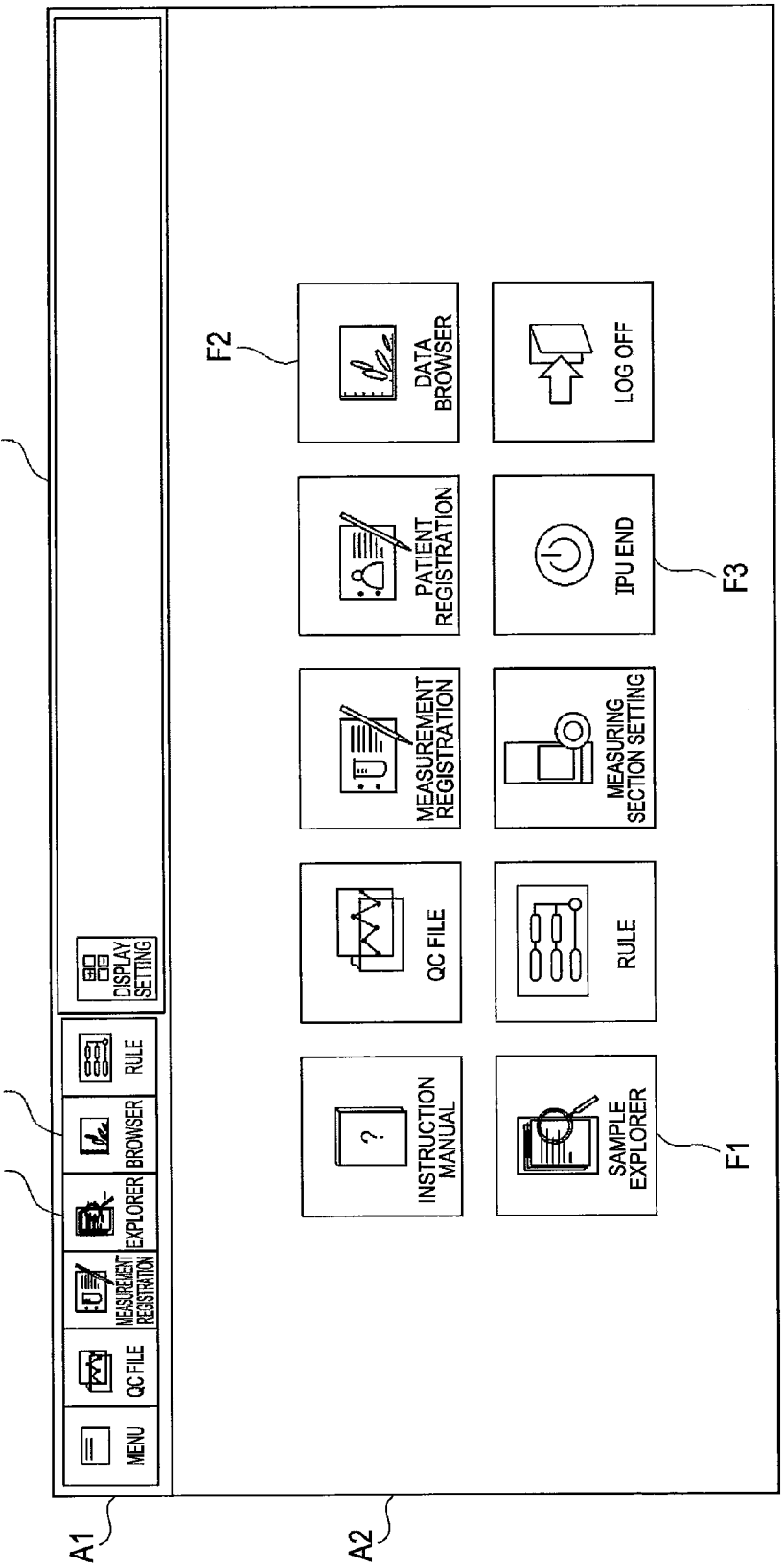
FIG. 10 is an illustrative view of a menu screen according to the embodiment.

FIG. 10 shows the menu screen D1. The menu screen D1 includes a tool bar display region A1 where a tool bar is displayed, and a main display region A2 where a plurality of icons for transitioning to other screens is displayed.

The tool bar display region A1 includes a sample explorer icon H1 for transitioning to a "sample explorer screen" for displaying in a list a plurality of measurement result records stored in the measurement result database DB1, and a data browser icon H2 for transitioning to a "data browser screen" for displaying in detail one of the plurality of measurement result records stored in the measurement result database DB1.

The main display region A2 includes a sample explorer icon F1 having the same function as the sample explorer icon H1, and a data browser icon F2. The main display region A2 also includes an end icon F3 for terminating the application program of the information processing unit 5.

Returning back to FIG. 8, the information processing unit 5 determines whether or not an instruction to display the sample explorer screen is input (step S202). The display instruction of the sample explorer screen can be input by clicking the sample explorer icons H1, F1 with a mouse in the menu screen of FIG. 10. If the display instruction of the sample explorer screen is not input (step S202: NO), the information processing unit 5 repeats the determination until receiving the display instruction. If determined that the display instruction is input (step S202: YES), the information processing unit 5 displays the sample explorer screen D2 shown in FIG. 11 on the display section 52.

Figure 11:
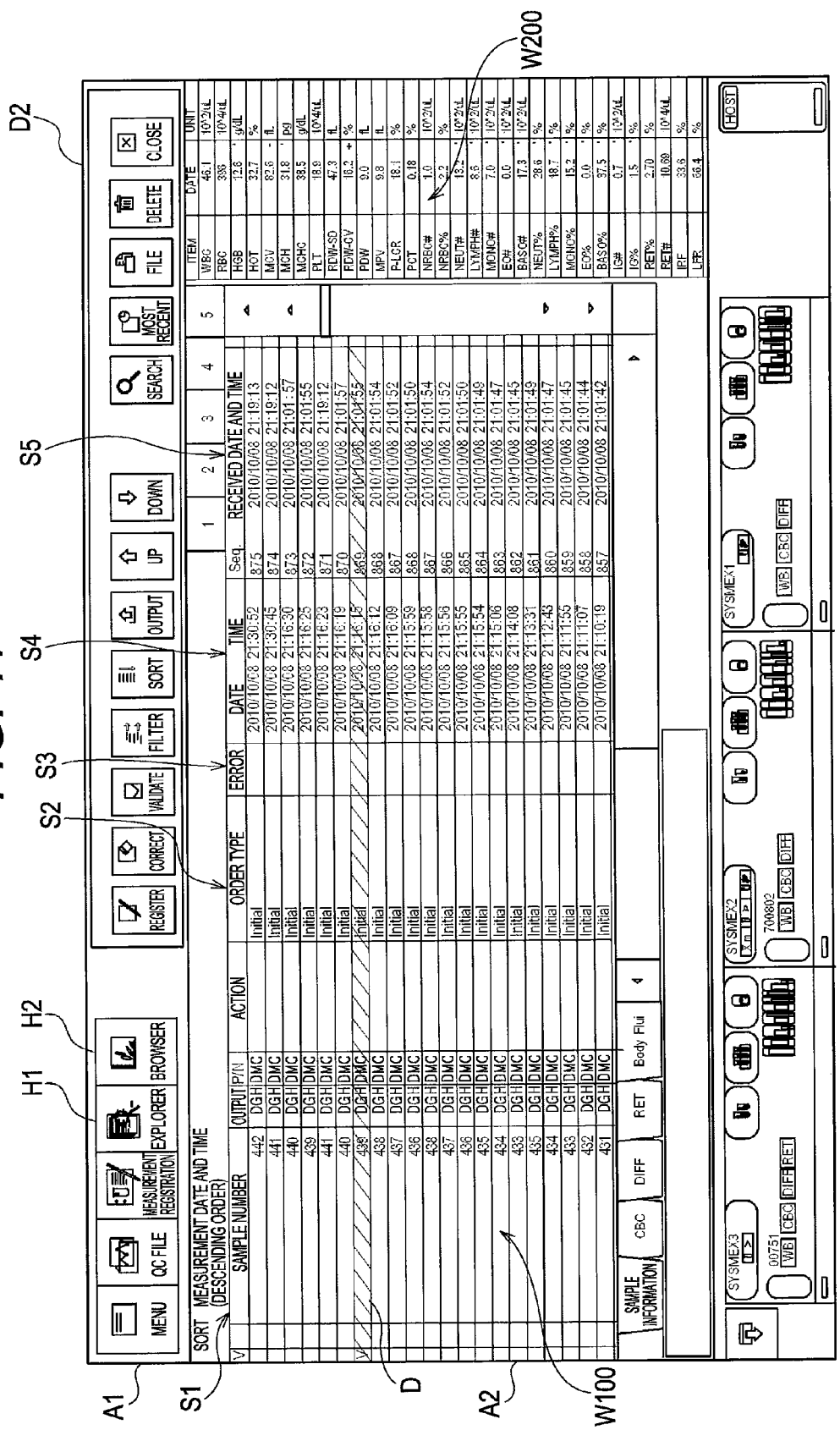
FIG. 11 is an illustrative view of a sample explorer screen according to the embodiment.

FIG. 11 shows the sample explorer screen D2. The sample explorer screen D2 includes the tool bar display region A1 and the main display region A2. The tool bar display region A1 has the same configuration as that of the menu screen D1 of FIG. 10, and thus the description thereof will be omitted.

The main display region A2 includes a sample list W100 in which a plurality of measurement result records stored in the measurement result database DB1 is displayed in a list, and a numerical value data list W200 displaying the numerical value data of the measurement result record selected in the sample list W100.

As shown in FIG. 11, the sample list W100 includes a sample ID field S1, an order type field S2, an error information field S3, a measurement date and time field S4, and a received date and time S5.

The information stored in the sample ID column C5 of FIG. 4 is displayed in the sample ID field S1. The information stored in the order type column C6 of FIG. 4 is displayed in the order type field S2. The information stored in the error information column C7 of FIG. 4 is displayed in the error information field S3. The information stored in the measurement date and time column C3 of FIG. 4 is displayed in the measurement date and time field S4. The information stored in the received date and time column C2 of FIG. 4 is displayed in the received date and time field S5.

The numerical value data list W200 displays in a list the numerical value data of the measurement result record selected in the sample list W100. Specifically, the information stored in the columns C9, C10, . . . of the measurement result record selected in the sample list W100 is displayed in the numerical value data list W200.

Each row of the sample list W100 can be selected by placing the cursor on an arbitrary row with the mouse and clicking. The sample explorer screen D2 can be closed by clicking a close icon at the upper right of the screen, where the screen returns to the menu screen D1 when the sample explorer screen D2 is closed.

With reference to FIG. 8, the information processing unit 5 determines whether or not a display instruction of the data browser screen D3 is received in the sample explorer screen D2 of FIG. 11 (step S204). The display instruction of the data browser screen D3 can be input by double clicking the data browser icon H2 with the mouse with the row of the measurement result to display selected in the sample list W100 in the sample explorer screen D2 of FIG. 11. The display instruction can also be input by double clicking the row of the measurement result to display in the sample list W100 with the mouse. Furthermore, it can be input by clicking the data browser icons H2, F2 with the mouse in the menu screen D1 of FIG. 10. In this case, the measurement result record with the most recent measurement date and time of the measurement result records stored in the measurement result database DB1 is assumed to be selected. Therefore, one measurement result record of the plurality of stored measurement result records is specified regardless of how the display instruction of the data browser screen D3 is input.

The information processing unit 5 proceeds to step S205 when determining that the display instruction of the data browser screen D3 is received (step S204: YES). The information processing unit 5 proceeds to step S208 when determined that the display instruction of the data browser screen D3 is not received (step S204: NO).

When determining that the display instruction of the data browser screen D3 is received (step S204: YES), the information processing unit 5 searches for the measurement result record including the same received date and time and the sample ID as the specified measurement result record (step S205). Specifically, the information processing unit 5 searches the measurement result list L100 of the measurement result database DB1 with the sample ID of the specified record as the search query, and extracts the measurement result record including the same sample ID from the measurement result list L100. Furthermore, the information processing unit 5 searches for the extracted measurement result record with the received date and time of the specified record as the search query, and extracts the measurement result record including the same received date and time as the specified record.

The information processing unit 5 then searches for the measurement result including the patient ID same as the specified measurement result record and including the received date and time different from the specified measurement result record (step S206). Specifically, the information processing unit 5 searches the measurement result list L100 of the measurement result database DB1 with the patient ID of the specified measurement result record as the search query, and extracts the measurement result record including the same patient ID from the measurement result list L100. Furthermore, the information processing unit 5 excludes the measurement result record including the received date and time of the specified measurement result record from the extracted measurement result records to extract only the measurement result record including the received date and time different from the specified record.

The information processing unit 5 displays the data browser screen D3 (step S207). This process will be described later.

The information processing unit 5 determines whether or not an instruction to end the display is input (step S208). The instruction to end the display can be input by clicking an IPU end icon F3 with the mouse in the menu screen D1. If determined that the instruction to end the display is input (step S208: YES), the information processing unit 5 ends the displaying process. If the instruction to end the display is not input (step S208: NO), the process returns to step S202.

The process of displaying the data browser screen will now be described with reference to the flowchart of FIG. 9 and the data browser screen of FIG. 12.

The information processing unit 5 displays the data browser screen (step S301). FIG. 9 shows the data browser screen D3. The data browser screen D3 is a screen for displaying detailed information of one specified measurement result record. The detailed information referred to herein is the information that is not displayed in the sample explorer screen D2, and specifically includes image data. In the present embodiment, the image data of the particle size distribution (histogram) of the red blood cells and the blood platelets created with the numerical value data, and the image data of the two-dimensional distribution diagram (scattergram) of the white blood cells correspond to the detailed information.

The data browser screen D3 includes the tool bar display region A1 and the main display region A2, similar to other screens.

Similar to the menu screen D1 and the sample explorer screen D2, a screen transitioning icon group including the sample explorer icon H1 and the data browser icon H2 is displayed in the tool bar display region A1. An operation icon group for executing operations on the measurement result being displayed is displayed adjacent to the screen transitioning icon. The operation icon group includes a correction icon N1 for correcting the information (patient's name, attending physician) of the measurement result record being displayed, a validation icon N2 for acknowledging (validating) the measurement result being displayed, and a close icon N3 for ending the data browser screen D3. A previous value button Y1 and a next value button Y2 are also displayed in the operation icon group. The functions of the previous value button Y1 and the next value button Y2 will be described later.

The detailed information of one measurement result is displayed in the main display region A2. In the example of FIG. 12, the main display region A2 includes a numerical value data region P, a flag region Q, and a graph region R. The numerical value data region P includes a CBC column P1 in which the numerical value data of the CBC item is displayed, a DIFF column P3 in which the numerical value data of the DIFF item is displayed, and a RET column P2 in which the numerical value data of the RET item is displayed. The flag region Q is a region in which the set flag is displayed when the flag is set as a result of the measurement, and includes a WBC flag column Q1 in which the flag associated with the white blood cells (WBC) is displayed, a RBC flag column Q2 in which the flag associated with the red blood cells (RBC) is displayed, and a PLT flag column Q3 in which the flag associated with the blood platelets (PLT) is displayed. The graph region R is a region in which the image contained in the measurement result is displayed, and includes a plurality of scattergrams R1, a histogram R2 of the red blood cells (RBC), and a histogram R3 of the blood platelet (PLT).

A sample link button display region X is arranged on the upper side of the main display region A2. In the example shown in FIG. 12, a plurality of sample link button groups X1 to X4 is displayed. In the data browser screen D3 shown in FIG. 12, the measurement result of "Initial" of the sample indicated with the sample ID: 439 in which a total of four measurements of "Initial", "Initial/Repeat", "Reflex", and "Reflex/Repeat" is carried out is shown. The sample link button is displayed by the number corresponding to the number of measurements of the sample, and thus four sample link buttons are displayed in the example shown in FIG. 12 according to the number of measurements, which is a total of four measurements. The sample link buttons X1 to X4 are corresponded to the measurement results of "Initial", "Initial/Repeat", "Reflex", and "Reflex/Repeat" of the sample ID: 439, respectively. More specifically describing, the sample link button X1 is a button for displaying the measurement result of "Initial" of the sample having the sample ID: 439. The sample link button X2 is a button for displaying the measurement result of "Initial/Repeat" of the sample having the sample ID: 439. The sample link button X3 is a button for displaying the measurement result of "Reflex" of the sample having the sample ID: 439. The sample link button X4 is a button for displaying the measurement result of "Reflex/Repeat" of the sample having the sample ID: 439. In the state shown in FIG. 12, the sample link button X1 is disabled. As will be described later, such buttons function as buttons for displaying the measurement result corresponded in advance in the main display region A2 by being clicked.

Each sample link button X1 to X4 includes order type of the corresponded measurement result, and identification information of the measurement units 2, 3 that executed the measurement, which is the basis of the corresponded measurement result. The user can know to which measurement result of the order type each button is corresponded by simply looking at the button, and can know which measurement unit executed the measurement that became the basis of the corresponded measurement result.

The sample link buttons X1 to X4 are lined as "Initial", "Initial/Repeat", "Reflex", and "Reflex/Repeat" in order from the left. This order is the same as the order in which the measurement is carried out with respect to one sample, as also apparent from FIG. 6. The user can browse through the measurement results along the order of measurement by clicking the sample link button in order from the left.

In the present embodiment, the initial test (measurement of "Initial") is always carried out once, and the re-measurement is carried out a maximum of three times. In corresponding thereto, at least one and a maximum of four sample link buttons are displayed. That is, the sample link button is displayed by the number corresponding to the number of measurements on one sample, and thus the user can know how many measurement results associated with the measurement result being displayed exist by simply looking at how many buttons are displayed in the sample link button display region X when the data browser is opened. In other words, the number of re-measurements can be known by counting the number of buttons displayed in the sample link button display region X.

Figure 12:
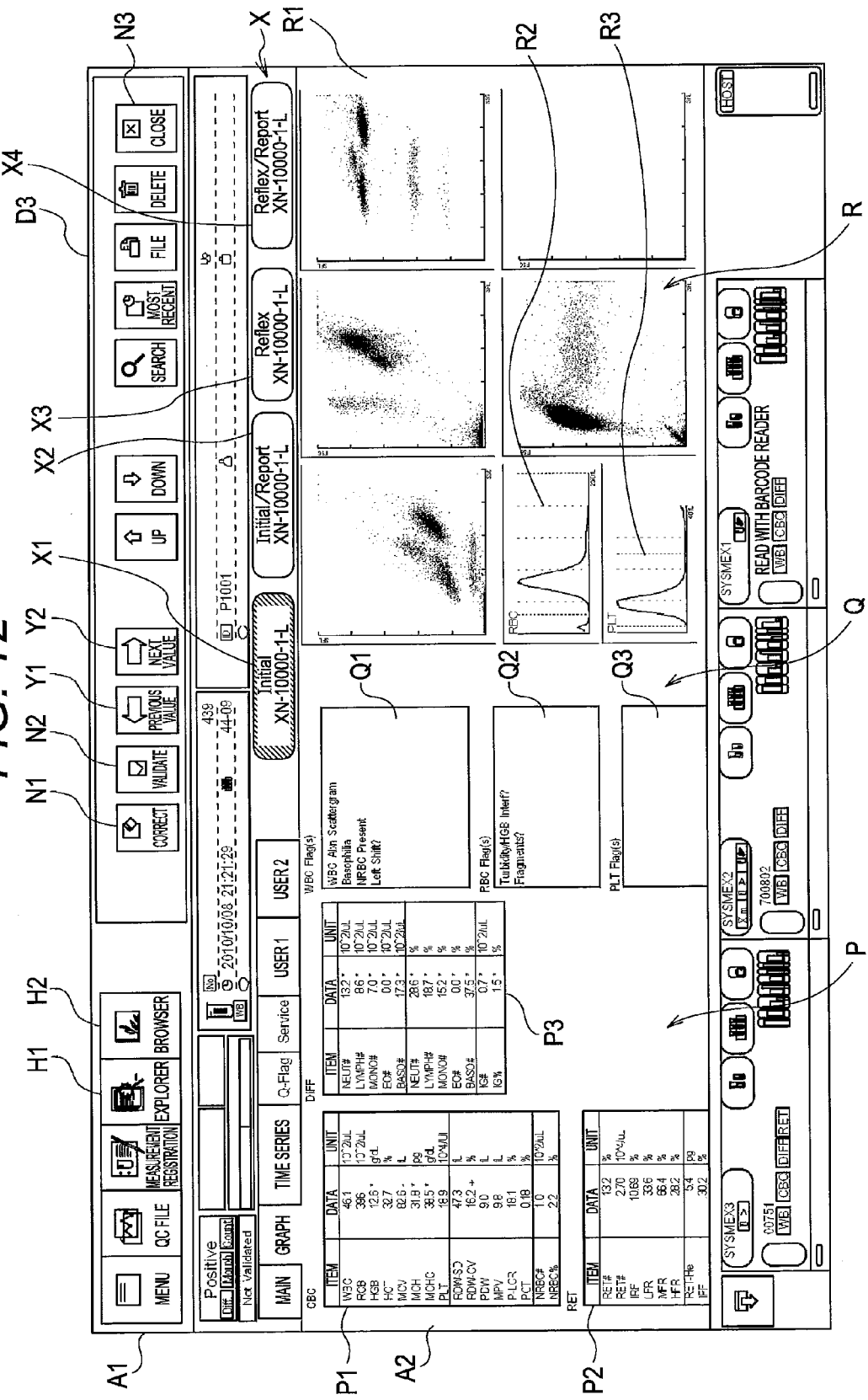
FIG. 12 is an illustrative view of a data browser screen according to the embodiment.

In the example shown in FIG. 12, the "Initial" button X1 is displayed in a different color from the other buttons X2 to X4 ("Initial" button X1 is shaded in the drawing to indicate that it is displayed in a different color). This indicates that the order type of the measurement result displayed in the main display region A2 is "Initial". As will be described later, when the other sample link buttons X2 to X4 are selected in the screen of FIG. 12, the measurement result corresponded in advance to the selected sample link button is displayed in the main display region A2, and only the selected sample link button is displayed in a different color. Therefore, the user can visually grasp which measurement result of the associated measurement results is being displayed in the main display region A2 when displaying the data browser screen.

Figure 9:
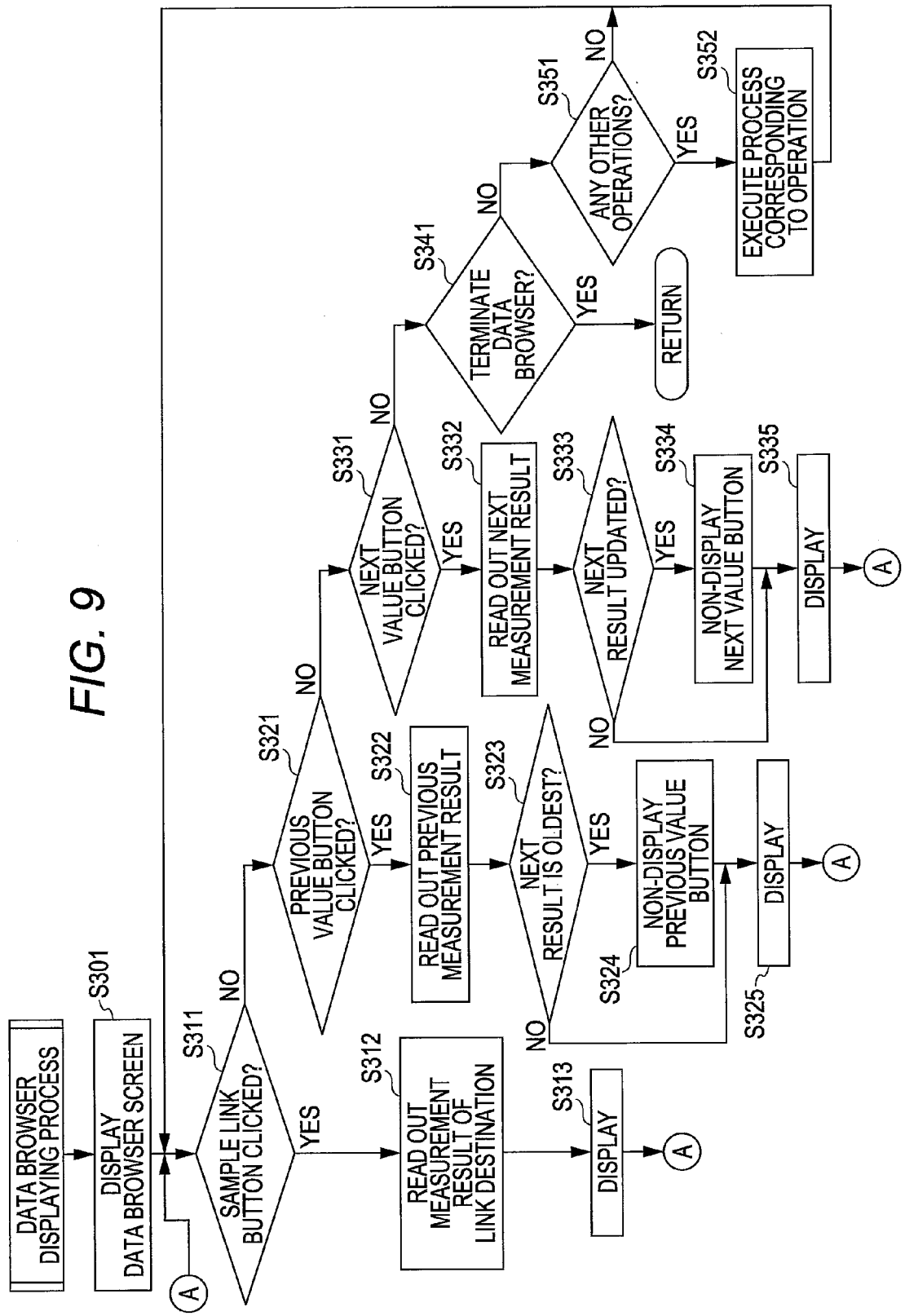
FIG. 9 is a flowchart showing a sub-routine of the flowchart of FIG. 8.

With reference to FIG. 9, the information processing unit 5 displays the data browser screen D3 (step S301). Specifically, the information processing unit 5 reads out the measurement result record specified in step S204 (see FIG. 8), and displays the information contained in the read measurement result record in each area of the main display region A2.

Furthermore, when the measurement result record having the same sample ID as the specified measurement result record is extracted as a result of the search in step S205 (see FIG. 8), the information processing unit 5 displays the sample link button corresponding to the extracted measurement result record.

For instance, with reference to FIG. 4, assume that the measurement result record (result ID: X1003) of "Initial" of the sample ID: 442 is specified and the display instruction of the data browser screen D3 is input. In this case, three records of the measurement result record (result ID: X1015) of "Initial/Repeat", the measurement result record (result ID: X1022) of "Reflex", and the measurement result record (result ID: X1030) of "Reflex/Repeat" are extracted as other measurement results including the sample ID: 442. In this case, therefore, a total of four sample link buttons are displayed, where each sample link button is displayed with "Initial", "Initial/Repeat", "Reflex", and "Reflex/Repeat". In this case, the extracted measurement result records all have the information stored in the unit information column C8 of "XN-10000-1-L", and thus "XN-10000-1-L" is displayed for all as the apparatus identification information of each sample link button. This state is shown in FIG. 12.

With reference to FIG. 4, assume that the measurement result (result ID: X1001) of the sample ID: 440 is specified, and the display instruction of the data browser screen D3 is input. In this case, the other measurement result records including the sample ID: 440 are not stored, that is, the sample of sample ID: 440 is a sample in which the re-measurement is not carried out, and thus the other measurement result records other than "Initial" are not extracted. In this case, therefore, only the sample link button of "Initial" is displayed on the data browser screen D3 of FIG. 12.

Furthermore, if the measurement result record having the same patient ID as the specified measurement result record is extracted as a result of searching in step S206 (see FIG. 8), the information processing unit 5 displays the previous value button/next value button in accordance with the extracted measurement result record.

With reference to FIG. 4, assume that the measurement result record of result ID: X4003 is specified, and the display instruction of the data browser screen D3 is input. In this case, two records of the measurement result record of result ID: X1002 and the measurement result record of result ID: 9600 are extracted as the measurement result records having the same patient ID.

The measurement result record of X1002 has a received date and time of before the specified measurement result record of X4003, and thus the measurement result record of X1002 corresponds to "previous value" with respect to the measurement result record of X4003. The measurement result record of X9600 has a received date and time of after the specified measurement result record of X4003, and thus the measurement result record of X9600 corresponds to "next value" with respect to the measurement result record of X4003.

In this case, therefore, the measurement result of X4003 is displayed in the main display region A2, and the previous value button Y1 for displaying the measurement result of X1002 and the next value button Y2 for displaying the measurement result of X9600 are displayed in the data browser screen D3.

With reference to FIG. 4, assume that the measurement result record of result ID: X1001 is specified and the display instruction of the data browser screen D3 is input. In this case, only one measurement result record of patient ID: P837 is stored, and hence the other measurement result records are not extracted, and the previous value button and the next value button are not displayed.

Assume that the measurement result record of result ID: X1003 is specified and the display instruction of the data browser screen D3 is input. In this case, three records of X1015, X1022, and X1030 exist other than X1003 for the measurement result records having the patient ID: P1001, but they all have the same received date and time, and thus do not correspond to "previous value"/"next value" with respect to the record of X1003. Therefore, such records are not extracted in the search process of step S206, and the previous value/next value buttons are not displayed.

The data browser screen D3 is displayed through the above processes.

The information processing unit 5 determines whether or not one of the sample link buttons X2 to X4 is clicked with the mouse (step S311). When one of the sample link buttons X2 to X4 is clicked (step S311: YES), the information processing unit 5 reads out the measurement result record corresponded in advance to the clicked sample link button from the measurement result database DB1 (step S312), and displays the read measurement result record on the main display region A2 (step S313). For instance, in the screen shown in FIG. 12, when the sample link button X3 is clicked, the information processing unit 5 reads out the measurement result record of "Reflex", and displays the measurement result in the main display region A2. In this case, the display color of the sample link button X3 is changed, and the display color of the sample link button X1 becomes a default.

If the sample link button is not clicked (step S311: NO), the information processing unit 5 determines whether or not the previous value button Y1 is clicked (step S321). If the previous value button Y1 is clicked (step S321: YES), the information processing unit 5 reads out the measurement result record corresponding to the previous value with respect to the measurement result being displayed from the measurement result database DB1 (step S322).

The information processing unit 5 then determines whether the measurement result record to be displayed next has the oldest received date and time among the measurement result records extracted in step S207 (step S323). In other words, the information processing unit 5 determines whether or not the measurement result record earlier than the record of the measurement result to be displayed next exists. If it is the oldest measurement result record (step S323: YES), the information processing unit 5 non-displays the previous value button Y1 (step S324). If it is not the oldest measurement result record (step S323: NO), the information processing unit 5 skips step S324.

The information processing unit 5 displays the measurement result record read out in step S322 on the main display region A2 (step S325).

If the previous value button Y1 is not clicked (step S321: NO), the information processing unit 5 determines whether or not the next value button Y2 is clicked (step S331). If the next value button Y2 is clicked (step S331: YES), the information processing unit 5 reads out the record of the measurement result corresponding to the next value with respect to the measurement result being displayed from the measurement result database DB1 (step S332).

The information processing unit 5 then determines whether the measurement result record to be displayed next has the newest received date and time among the measurement result records extracted in step S207 (step S333). In other words, the information processing unit 5 determines whether or not the measurement result record later than the record of the measurement result to be displayed next exists. If it is the newest measurement result record (step S333: YES), the information processing unit 5 non-displays the next value button Y2 (step S334). If it is not the newest measurement result record (step S333: NO), the information processing unit 5 skips step S334.

The information processing unit 5 displays the measurement result record read out in step S332 on the main display region A2 (step S335).

The processes of steps S321 to 325 and steps S331 to 335 will be described with reference to FIG. 4. Assume that the measurement result of the record of the result ID: X4003 of FIG. 4 is displayed in the main display region A2 of FIG. 12. The measurement result record of result ID: X4003 includes X1002 for the previous value and X9600 for the next value. When the previous value button Y1 is clicked (step S321), the measurement result record of X1002 is read out as the previous value (step S322). X1002 is the measurement result record of the oldest received date and time in the measurement result records including the patient ID: P37, and thus the earlier measurement result record does not exist. Therefore, step S323 becomes YES, and the previous value button Y1 is not displayed in the data browser screen D3 of X1002. Similarly, when the next value button Y2 is clicked (step S331), the measurement result record of X9600 is read out as the next value (step S332). X9600 is the measurement result record of the newest received date and time in the measurement result records including the patient ID: P37, and thus the later measurement result record does not exist. Therefore, step S333 becomes YES, and the previous value button Y1 is not displayed in the data browser screen D3 of X1002.

As the previous value button Y1 is not displayed when displaying the oldest measurement result, and the next value button Y2 is not displayed when displaying the newest measurement result, the user can know if the measurement result currently being displayed is the newest measurement result or the oldest measurement result by simply looking at whether the previous value button Y1 and the next value button Y2 are displayed.

If the next value button Y2 is not clicked (step S331: NO), the information processing unit 5 determines whether or not an operation to terminate the data browser screen D3 is carried out (step S341). The operation for terminating the data browser screen D3 can be carried out by clicking the "close" icon N3 included in the screen transition icon group. When the terminating operation is performed (step S341: YES), the information processing unit 5 closes the data browser screen D3 and transitions the screen to the menu screen D1 or the sample explorer screen D2.

When the operation to terminate the data browser screen D3 is not performed (step S341: NO), the information processing unit determines whether or not the operation is performed on the data browser screen D3 (step S351), and carries out the process corresponding to the operation if the operation is performed (step S351: YES). For instance, if the correction icon N1 is clicked, a dialogue for inputting the changing content of the information of the measurement result being displayed is displayed, and the stored patient information is changed and the screen is updated when the change is confirmed. If the validate icon N2 is clicked, the measurement result being displayed is acknowledged (validated), and the measurement result is transmitted to the host computer HC. If the operation is not performed (step S351: NO), the process returns to step S311.

According to the present embodiment, the measurement result ("Initial/Repeat" etc.) of the re-measurement of the same sample can be displayed by simply clicking the sample link button when browsing the measurement result ("Initial") of the initial measurement of the sample in which re-measurement is carried out in the data browser screen D3. Therefore, according to the present embodiment, the operations of once closing the data browser screen D3 to return to the sample explorer screen D2, inputting the sample ID in the search box to search or sorting the measurement results displayed in a list are unnecessary to display the measurement result of the re-measurement from a state in which the measurement result of the initial measurement is displayed, whereby the operability can be enhanced.

According to the present embodiment, when the instruction to display the data browser screen D3 is input, other measurement results including the same sample ID are searched and the sample link buttons corresponded to the relevant other measurement results are displayed only when the other measurement results are stored. The user thus can recognize that the other measurement results including the same sample ID as the measurement result displayed in the data browser screen are stored by simply checking the presence/absence of the display of the sample link buttons. Therefore, when the measurement result of the initial measurement is displayed, whether the sample of the measurement result being displayed is the sample in which the measurement is carried out at least two or more times or the sample in which the measurement is carried out only once can be recognized by checking whether or not the sample link button corresponded to the measurement result of the re-measurement is displayed. Furthermore, the sample link button is displayed by the number corresponding to the number of measurements, and hence how many times the measurement is carried out for the sample of the measurement result being displayed can be recognized by simply counting the number of sample link buttons.

In the present embodiment, the sample link button corresponding to the measurement result displayed in the main display region A2 of the data browser screen D3 is displayed in a display format different from the other sample link buttons. Thus, to which one of the plurality of sample link buttons the measurement result currently displayed in the data browser screen is corresponded can be recognized at a glance.

In the present embodiment, the plurality of sample link buttons are displayed in a line from the left in the order the measurement of the measurement result corresponded to the respective button is carried out. Therefore, the measurement result can be browsed in the order of the measurement by clicking the sample link buttons in order from the left, and hence the operability enhances for the user.

In the present embodiment, the identification information of the measurement unit that carried out the measurement, which is the basis of the measurement result corresponded to the respective button, is displayed in the sample link button. The user thus can grasp the measurement unit that carried out the measurement by simply looking at the sample link button.

The error occurrence frequency and the measurement sensitivity of when the measurement is carried out differ depending on the measurement units. Thus, recognizing in which measurement unit the measurement result where error occurred is measured when referencing the data browser screen is an important element in knowing the cause of occurrence of error. If there is a difference in the measurement result between the first measurement and the second measurement when the same measurement item is re-measured, the influence of measurement sensitivity of the measurement unit is presumed. Therefore, information useful for the user can be provided by displaying the identification information of the measurement unit with the sample link button.

According to the present embodiment, when browsing one measurement result in the data browser screen D3, the measurement result of another sample collected from the same patient as the sample of the measurement result being displayed can be displayed by simply clicking the previous value button or the next value button.

According to the present embodiment, when the instruction to display the data browser screen D3 is input, other measurement results including the same patient ID are searched, and the previous value/next value buttons are displayed only when the other measurement results are stored. Therefore, the user can recognize whether the other measurement results of the same patient ID as the measurement result being displayed in the data browser screen exist by simply looking at whether or not the previous value/next value button is displayed.

According to the present embodiment, the measurement result in which the measurement is carried out immediately before of the measurement results including the same patient ID as the measurement result being displayed is displayed when the previous value button is clicked. The measurement result in which the measurement is carried out immediately after of the measurement results including the same patient ID as the measurement result being displayed is displayed when the next value button is clicked. Therefore, the measurement results can be browsed along a time series by simply clicking the previous value/next value buttons.

In the present embodiment, the previous value button is non-displayed if the measurement result displayed in the data browser screen D3 is the oldest measurement result of the measurement results of the same patient ID, and the next value button is non-displayed if the measurement result displayed in the data browser screen D3 is the newest measurement result of the measurement results of the same patient ID. Therefore, whether the measurement result being displayed is the oldest measurement result or the newest measurement result can be easily recognized by simply looking at whether the previous value/next value button is displayed.

Description of other Embodiments

The present invention is not limited to the above embodiment, and various modifications may be made.

Figure 13:
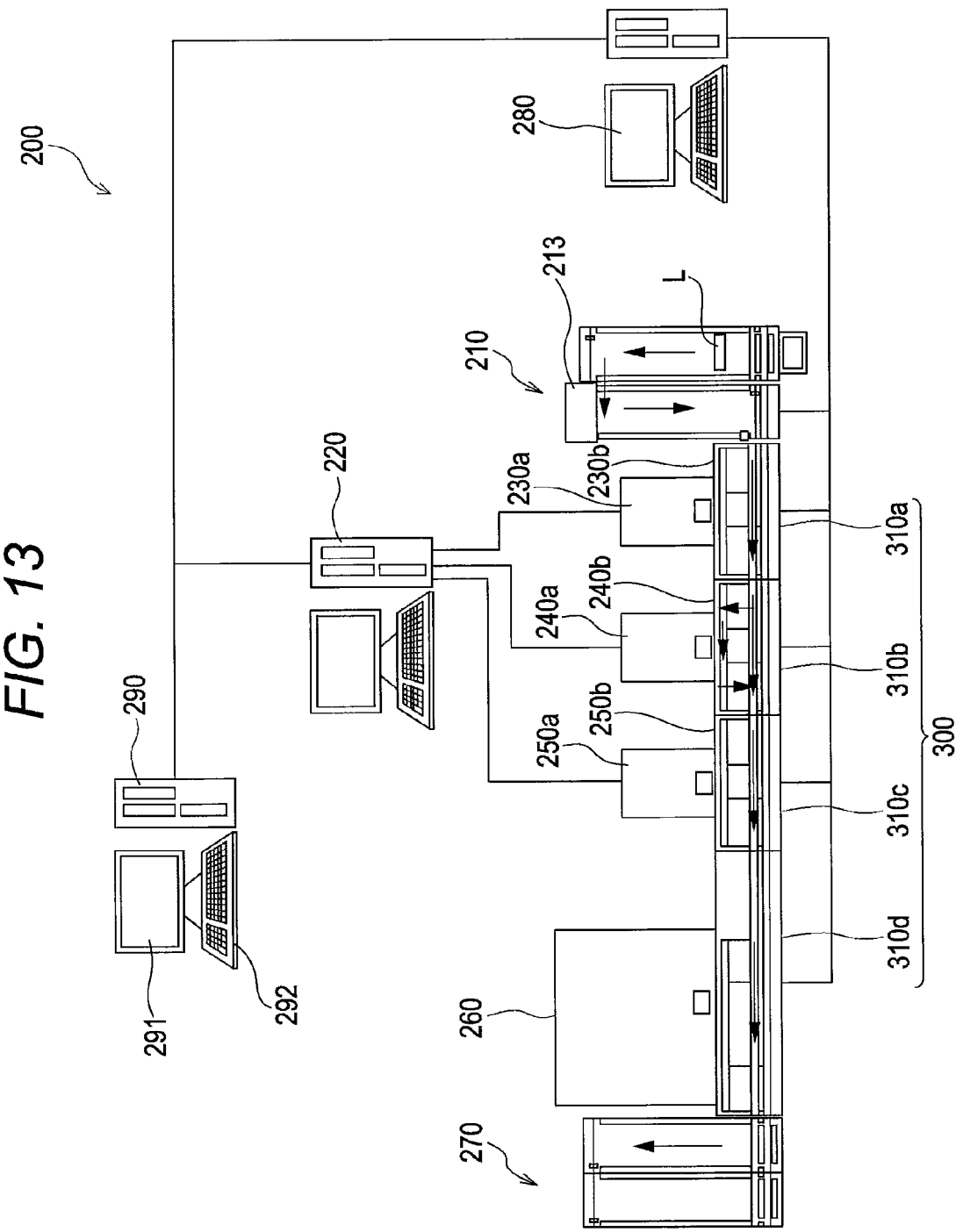
FIG. 13 is a schematic plan view of a sample analyzing system according to another embodiment.

FIG. 13 is a schematic plan view showing an overall configuration of a sample analyzing system according to another embodiment. In the sample analyzing system of the present embodiment, the host computer 290 unifies the management of the measurement results obtained from the plurality of measurement units, different from the embodiment described above. The host computer 290 has a configuration similar to the configuration of the information processing unit 5 shown in FIG. 3, and can cause a display section 291 to display the measurement result stored in the measurement result database DB1 arranged in the host computer 290 when the operator operates an input section 292.

As shown in FIG. 13, the sample analyzing system 200 includes a sample sending unit 210, a transport unit 300, measurement units 230a, 240a, 250a, a smear creating unit 260, an information processing unit 220, a sample collecting unit 270, and a system control unit 280. The information processing unit 220 and the system control unit 280 are communicably connected to the host computer 290 through a communication network.

The transport unit 3 includes transport lines 310a, 310b, 310c, and 310d, which transport lines 310a, 310b, 310c and 310d are connected in series to each other so as to extend in a lateral direction in the figure. The measurement unit 230a and a sampler 230b for supplying the sample to the measurement unit 230a are arranged on the back side of the transport line 310a. The measurement unit 240a and a sampler 240b for supplying the sample to the measurement unit 240a are arranged on the back side of the transport line 310b. The measurement unit 250a and a sampler 250b for supplying the sample to the measurement unit 250a are arranged on the back side of the transport line 310c. Furthermore, the smear creating unit 260 is arranged on the back side of the transport line 310d. The measurement units 230a, 240a, 250a have configurations similar to the measurement unit 2(3) of the first embodiment. The samplers 230b, 240b, 250b have a configuration similar to the sample transport unit 4 of the first embodiment other than having the function of carrying in the sample rack L from the transport line and the function of carrying out the sample rack L from the sample transport unit 4 to the transport line.

In the sample processing system 1, the sample rack L containing a plurality of sample containers T is set in the sample sending unit 210 by the operator. The sample rack L set in a rack accommodating section 201 is carried out from the sample sending unit 210 through a path shown with an arrow in the figure, and collected by the sample collecting unit 7 through the transport lines 310a, 310b, 310c, and 310d. The sample sending unit 210 includes a barcode reader 213 to read the barcode of the sample container T held in the sample rack L set in the sample sending unit 210. The read barcode information is transmitted to a system control unit 280.

The system control unit 280 transmits the received barcode information to the host computer 290 and inquires the measurement order. When receiving the inquiry of the measurement order, the host computer 290 determines the measurement order based on the sample ID contained in the barcode information, and transmits the same to the system control unit 280. When receiving the measurement order, the system control unit 280 determines the transporting destination of the sample rack L from the measurement units 230a, 240a, 250a, and the smear creating unit 260 based on the received measurement order. After determining the transporting destination, the system control unit 280 controls the transport unit 300 to transport the sample rack L to the transport line arranged in correspondence with the unit (apparatus) of the relevant transporting destination. A case in which the measurement unit 240a is determined for the transporting destination will be illustrated and described below.

The system control unit 280 controls the transport unit 300 to transport the sample rack L to the transport line 310b when transporting the sample rack L to the measurement unit 240a. When the sample rack L arrives at the transport line 310b, the system control unit 280 carries in the sample rack L from the transport line 310b to the sampler 240b. The sampler 240b carries in the sample rack L to the sampler 240b as shown with an arrow, supplies the sample rack L to the measurement unit 240a, and again carries out the sample rack L to the transport line 310b.

The measurement unit 240a aspirates the sample from the sample container T held in the supplied sample rack L, and executes the initial measurement. The measurement data obtained by measuring the sample with the measurement unit 240a is provided to the information processing unit 220. The information processing unit 220 analyzes the measurement data and transmits the measurement result to the host computer 290. The host computer 290 stores the received measurement result in the measurement result database DB1 with the order type of "Initial".

The host computer 290 stores the measurement result and also determines the necessity of re-measurement of the sample based on the received measurement result. If determined that re-measurement is necessary, the host computer 290 generates an additional order to carry out the re-measurement. When the additional order is generated, the host computer 290 transmits the additional order to the system control unit 280. When receiving the additional order, the system control unit 280 determines the transporting destination based on the received additional order information. Assume that the measurement unit 250a arranged on the downstream side of the measurement unit 240a is determined as the transporting destination.

When transporting the sample rack L to the measurement unit 250a, the system control unit 280 controls the transport unit 300 to transport the sample rack L to the transport line 310c. When the sample rack L arrives at the transport line 310cb, the system control unit 280 carries in the sample rack L from the transport line 310b to the sampler 250b. The sampler 250b carries in the sample rack L, supplies the sample rack L to the measurement unit 250a, and again carries out the sample rack L to the transport line 310c.

The measurement unit 250a aspirates the sample from the sample container T held in the supplied sample rack L, and executes the re-measurement. The measurement data obtained by measuring the sample with the measurement unit 250a is provided to the information processing unit 220. The information processing unit 220 analyzes the measurement data and transmits the measurement result to the host computer 290. The host computer 290 stores the received measurement result in the measurement result database DB1 with the type of additional order. The measurement results are accumulated in the measurement result database DB1 of the host computer 290 through the processes described above. The host computer 290 can cause the display section 291 to display the measurement result stored in the measurement result database DB1 when the operator operates the input section 292.

In the example shown in FIG. 13, one information processing unit 220 intensively performs the information processing on the measurement data from the plurality of measurement units, but the information processing unit 220 may be arranged in plurals.

In the embodiment described above, the measurement result is stored in any one of the computers, but a cloud server for intensively managing the measurement results may be arranged, and the measurement results stored in the cloud server may be browsed from the computer when referencing the measurement results.

A configuration in which the sample analyzer automatically executes the re-measurement has been described in the above embodiments, but this is not the sole case. For instance, the sample analyzer may measure the set sample rack only once, where when determined that re-measurement is necessary as a result of the user referencing the measurement result, the user may manually input the order of re-measurement to execute the re-measurement.

Figure 14:
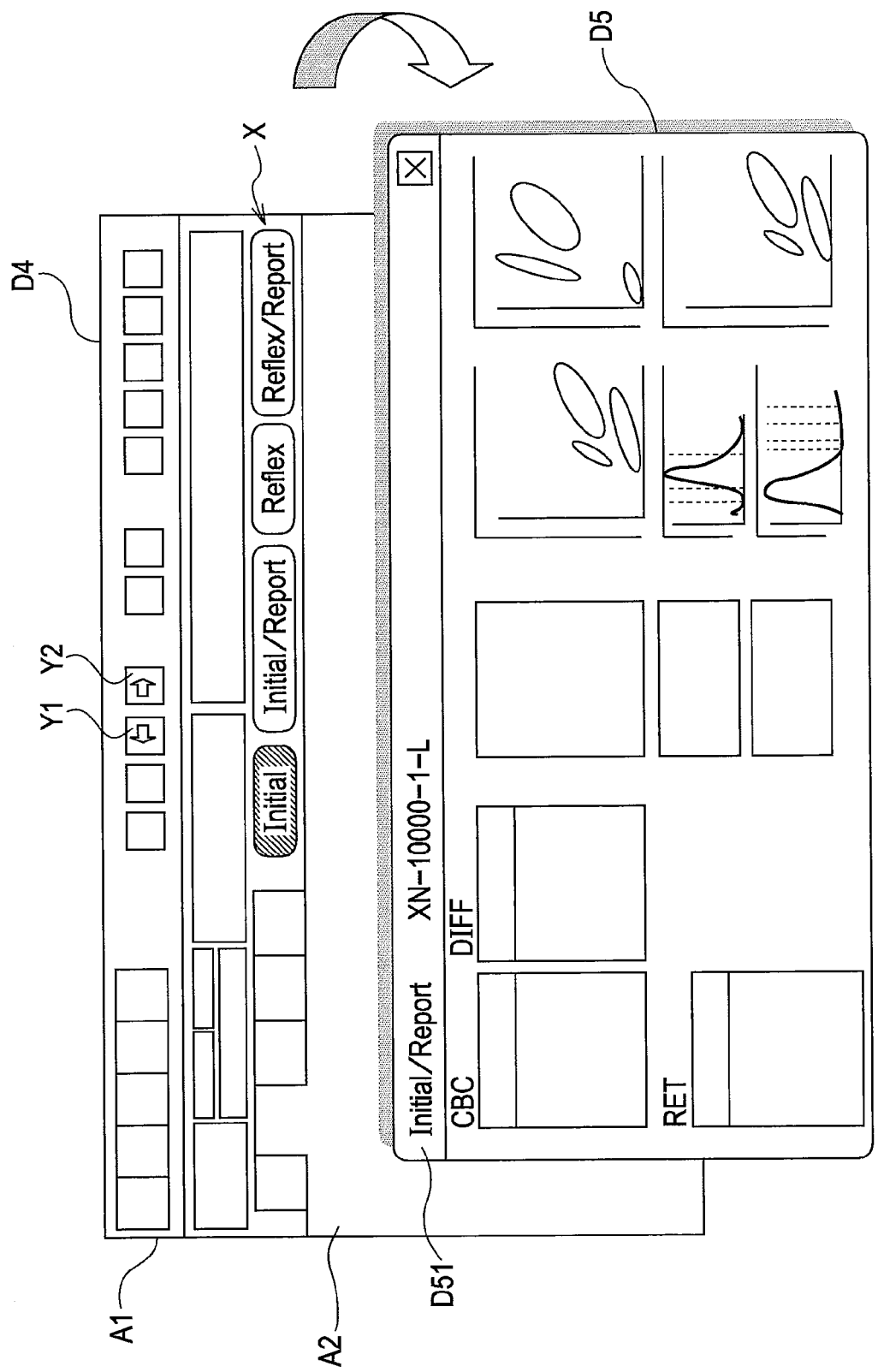
FIG. 14 is an illustrative view of a data browser screen according to another embodiment.

In the embodiment described above, a configuration in which the measurement result displayed in the main display region A2 is switched when the sample link button X or the previous value/next value button Y is clicked is illustrated, but is not limited thereto. For instance, a configuration in which the measurement result corresponded in advance to the sample link button is popup displayed may be adopted. This mode will be described with reference to FIG. 14. FIG. 14 is a view showing a variant of the data browser screen. The configuration of the data browser screen D4 is a configuration substantially the same as the data browse screen of FIG. 12, and thus the detailed description will be omitted.

Assume that the measurement result of "Initial" corresponding to the sample link button X1 is displayed in the main display region A2 with reference to FIG. 14. When the sample link button X2 is clicked in this state, a different window D5 displaying the measurement result of "Initial/Repeat", which is the measurement result corresponded in advance to the sample link button X2, is popup displayed. The title bar D51 arranged at the upper part of the window D5 displays the order type of the measurement result being displayed and the identification number of the measurement unit that executed the measurement. From which measurement the measurement result displayed in the window D5 is from can be grasped at a glance.

The window D5 can be displayed a maximum of three by clicking the sample link button X of the data browser screen D4. Each window can be displayed in a superimposed manner, and each measurement result can be displayed side by side.

A case in which the sample link button X is clicked has been described by way of example, but a different window is similarly popup displayed when the previous value button Y1 and the next value button Y2 is clicked.

In the embodiment described above, an example of measuring the additional measurement items in addition to the measurement item of "Initial" or "Initial/Repeat" when measuring "Reflex" has been described. This is not the sole case, and only the additional measurement may be measured when measuring "Reflex".

In the embodiment described above, "Rerun" is measured if the measurement result contains an abnormal numerical value, and "Reflex" is measured if the numerical value in the measurement result is within a predetermined numerical value range, but various conditions can be set for the conditions of determining whether or not re-measurement is necessary, and are not particularly limited. For instance, the user may arbitrarily set the numerical value range. The conditions of re-measurement are not limited to the numerical value range. For instance, when the measurement result of a certain sample is obtained, the past sample collected from the same patient as the relevant sample may be searched from the measurement result database for comparison, and determination may be made that re-measurement is necessary if a significant difference is detected in the two measurement results. Furthermore, instead of the numerical value data, the pattern of the scattergram or the histogram may be analyzed, and the necessity of the re-measurement may be determined based on the analysis result.

In the embodiment described above, a mode of displaying the sample link button on the data browse screen D3 in an overlapping manner is shown, but is not limited thereto. For instance, the sample link button may be displayed outside the screen of the data browser screen D3.

In the embodiment described above, an example in which the sample link button is provided to input the display instruction of other measurement results has been described, but a predetermined character string may be displayed in place of the sample link button, and a hyperlink may be set thereto.

In the embodiment described above, a mode in which the display instruction of the measurement result corresponded in advance to the sample link button is input when the sample link button is clicked on the screen has been described, but the display instruction is not limited to being input from the screen. For instance, a message related to the operation for displaying the associated measurement result may be displayed with the data browser screen D3, and the associated measurement result may be displayed when the operation described in the message is performed.

Figure 15A:
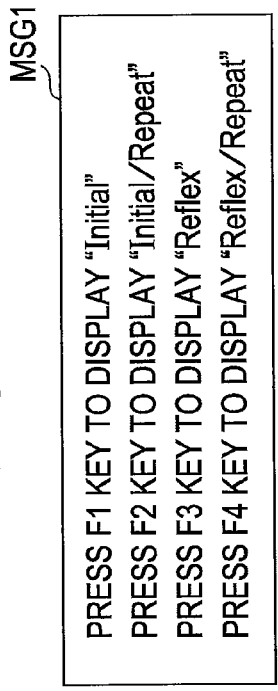
FIGS. 15A and 15B are views describing an input method of a display instruction according to another embodiment.
Figure 15B:
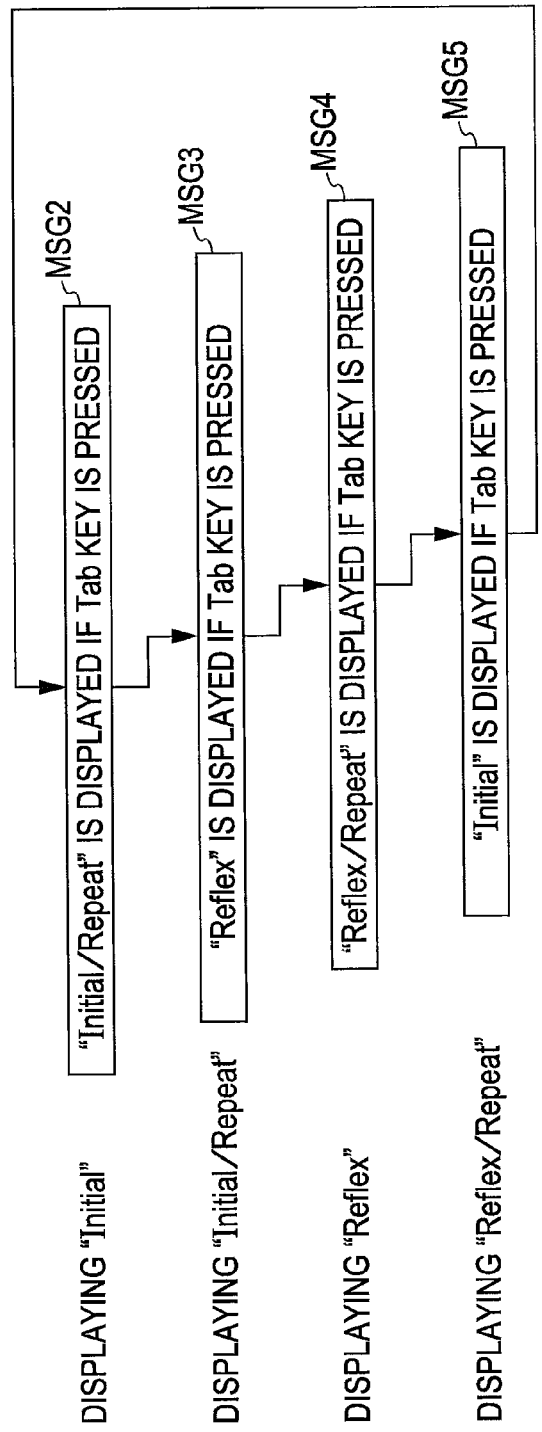

One example of such mode will be described with reference to FIG. 15. FIG. 15(a) is a view showing one example of a message displayed on the data browser screen. FIG. 15(b) is a view schematically showing the message displayed on the data browser screen along the order the display is switched.

In this mode, a specific key of the keyboard is assigned to each of the other measurement results associated with the one measurement result in advance, and a message MSG1 of FIG. 15(a) is displayed with the data browser screen D3. When the specific key input is received, the measurement result corresponding to the input key is displayed. In the example of FIG. 15(a), when the F2 key assigned to "Initial/Repeat" is pressed, the data browser screen of the measurement result of "Initial/Repeat" is displayed. When the F3 key assigned to "Reflex" is pressed, the data browser screen of the measurement result of "Reflex" is displayed.

In another mode, the message of FIG. 15(b) is displayed with the data browser screen D3. When the key input of a specific key (Tab key) is received, the measurement results to display are sequentially switched. Describing with reference to FIG. 15(b), a message MSG2 is displayed when the measurement result of "Initial" is being displayed on the data browser screen. When the Tab key is pressed with the message MSG2 being displayed, the measurement result of "Initial/Repeat" is displayed on the data browser screen, and the message MSG2 switches to a message MSG3. Thus, the measurement results to display are switched in the order of "Initial", "Initial/Repeat", "Reflex", "Reflex/Repeat" every time the Tab key is pressed, and the message to be displayed is also switched therewith.

In the embodiment described above, the blood analyzer has been described by way of example, but the present invention can be widely applied to apparatus for analyzing a clinical sample collected from a patient. For instance, application can be made to a urine analyzer, an immune analyzer, a coagulation time measurement apparatus, a biochemical analyzer, and the like.

What is claimed is:

1. A data management computer for a sample measuring apparatus comprising:
   a data storage for storing results of measurements for a sample obtained by the sample measuring apparatus, the measurements including an initial measurement for the sample and a secondary measurement which is performed on the sample following the initial measurement;
   a display section;
   an input device; and
   a controller programmed to:
   cause the display section to display a first result screen which shows a result of the initial measurement for a sample;
   receive a predefined operation by use of the input device while displaying the first result screen; and
   cause the display section to display, in a response to the predefined operation, a second result screen which shows a result of the secondary measurement for the sample, wherein
   the first result screen includes a first character and/or figure indicating that the result of secondary measurement for the sample is stored in the data storage and a second character and/or figure indicating that the result of the initial measurement is on display.

2. The data management computer according to claim 1, wherein the controller causes the display section to display an object for receiving an instruction to display the second result screen with the first result screen.

3. The data management computer according to claim 1, wherein the controller causes the display section to display an object for receiving an instruction to display the first result screen with the second result screen, and the controller causes the display section to display the first result screen when the object is operated by use of the input device.

4. The data management computer according to claim 1, wherein the controller causes the display section to display the second result screen when the first character and/or figure is operated by use of the input device.

5. The data management computer according to claim 1, wherein the data management computer is connected to a plurality of sample measuring apparatuses;
   the first character and/or figure includes a character for identifying one of the sample measuring apparatuses that carried out the secondary measurement, and
   the second character and/or figure includes a character for identifying one of the measuring apparatuses that carried out the initial measurement.

6. The data management computer according to claim 1, wherein the data storage also stores a result of a tertiary measurement for the sample; and
   the controller causes, when displaying the first result screen, the display section to display an object for receiving an instruction to display the second result screen and an object for receiving an instruction to display a third result screen which shows a result of the tertiary measurement, and
   the controller causes the display section to display, in a response to the instruction, the second or third result screen corresponds to the received instruction.

7. The data management computer according to claim 6, wherein the first result screen includes:
   a third character and/or figure indicating that the result of the tertiary measurement for the sample is stored in the data storage.

8. The data management computer according to claim 7, wherein the controller causes the display section to display the second result screen when the first character and/or figure is operated by use of the input device, and
   the controller causes the display section to display the third result screen when the third character and/or figure is operated by use of the input device.

9. The data management computer according to claim 7, wherein
   the first to third characters and/or figures are displayed in a line in order the corresponding measurement was carried out.

10. The data management computer according to claim 9, wherein the character and/or figure corresponding to the measurement result being on display is displayed in a display format different from other characters and/or figures.

11. The data management computer according to claim 1, wherein the first result screen does not include the result of secondary measurement, and the second result screen does not include the result of the initial measurement.

12. The data management computer according to claim 1, wherein the result screen includes at least a numerical list region and a distribution diagram region, the numerical list region including numerical values for a plurality of measurement items, and the distribution diagram region including a distribution diagram of a component contained in the sample.

13. The data management computer according to claim 1, wherein when the measurement result of a sample received from the measuring apparatus satisfies a predetermined condition, the controller automatically transmits to the measuring apparatus an instruction to carry out the secondary measurement.

14. The data management computer according to claim 1, wherein the controller causes the display section to display a message related to an operation for displaying the secondary measurement with the first result screen.

15. A sample analyzing system comprising:
one or more sample measuring apparatuses for measuring a sample;
a first computer that includes a data storage device for storing results of measurements for the sample obtained by the sample measuring apparatus, the measurements including an initial measurement for the sample and a secondary measurement which is performed on the sample following the initial measurement;
a data management computer communicably connected to the first computer, wherein
the data management computer includes a display section; an input device; and a controller which is programmed to:
cause the display section to display a first result screen which shows a result of the initial measurement for the sample, wherein the first result screen includes an object for receiving an instruction to display a second result screen which shows a result of the secondary measurement for the sample with the first result screen;
receive the instruction by use of the input device while displaying the first result screen; and
cause the display section to display, in a response to the instruction, the second result screen, wherein
the result screen includes at least a numerical list region and a distribution diagram region, the numerical list region including numerical values for a plurality of measurement items, and the distribution diagram region including a distribution diagram of a component contained in the sample.

16. A sample analyzing system according to claim 15, wherein the numerical list region includes a CBC column in which the numerical value date of the CBC item is displayed, a Diff column in which the numerical value date of the Diff item is displayed, and a RET column in which the numerical value date of the RET item is displayed, and the distribution diagram region includes a plurality of scattergrams, a histogram of red blood cell, and a histogram of the blood platelet.

17. A computer program product for causing a computer including an input device and a display section to function as a data management computer for a sample measuring apparatus, the computer program product comprising:
a computer readable medium; and
instruction code stored in the computer readable medium, wherein the instruction code is executable by the computer to cause the computer to perform acts comprising:
causing the display section to display a first result screen which shows a result of an initial measurement for a sample, wherein the first result screen includes an object for receiving an instruction to display a second result screen which shows a result of a secondary measurement for the sample with the first result screen;
receiving the instruction to display the second result screen via an input device while displaying the first result screen; and
causing the display section to display, in a response to a predefined operation, the second result screen, wherein
the result screen includes at least a numerical list region and a distribution diagram region, the numerical list region including numerical values for a plurality of measurement items, and the distribution diagram region including a distribution diagram of a component contained in the sample.

18. A computer program product according to claim 17, wherein the numerical list region includes a CBC column in which the numerical value date of the CBC item is displayed, a Diff column in which the numerical value date of the Diff item is displayed, and a RET column in which the numerical value date of the RET item is displayed, and the distribution diagram region includes a plurality of scattergrams, a histogram of red blood cell, and a histogram of the blood platelet.

19. A data management computer for a sample measuring apparatus comprising:
a data storage for storing results of measurements for a sample obtained by the sample measuring apparatus, the measurements including an initial measurement for the sample and a secondary measurement which is performed on the sample following the initial measurement;
a display section;
an input device; and
a controller programmed to:
cause the display section to display a first result screen which shows a result of the initial measurement for the sample, wherein the first result screen includes an object for receiving an instruction to display a second result screen which shows a result of the secondary measurement for the sample with the first result screen;
receive the instruction by use of the input device while displaying the first result screen; and
cause the display section to display, in a response to the instruction, the second result screen, wherein
the result screen includes at least a numerical list region and a distribution diagram region, the numerical list region including numerical values for a plurality of measurement items, and the distribution diagram region including a distribution diagram of a component contained in the sample.

20. The data management computer according to claim 19, wherein the numerical list region includes a CBC column in which the numerical value date of the CBC item is displayed, a Diff column in which the numerical value date of the Diff item is displayed, and a RET column in which the numerical value date of the RET item is displayed, and the distribution diagram region includes a plurality of scattergrams, a histogram of red blood cell, and a histogram of the blood platelet.

21. A data management computer for a sample measuring apparatus comprising:
a data storage for storing results of measurements for a sample obtained by the sample measuring apparatus, the measurements including an initial measurement for the sample and a secondary measurement which is performed on the sample following the initial measurement;

a display section;

an input device; and a controller programmed to:

cause the display section to display a first result screen which shows a result of the initial measurement for the sample, wherein the first result screen includes an object for receiving an instruction to display a second result screen which shows a result of the secondary measurement for the sample with the first result screen;

receive the instruction by use of the input device while displaying in the first result screen; and cause the display section to display, in a response to the instruction, the second result screen, wherein when the measurement result of the sample received from the measuring apparatus satisfies a predetermined condition, the controller automatically transmits to the measuring apparatus an instruction to carry out the secondary measurement.

22. The data management computer according to claim 21, wherein the predetermined condition is whether error occurs or not in the measurement results of the sample.

23. A sample analyzing system comprising:

one or more sample measuring apparatuses for measuring a sample;

a first computer that includes a data storage for storing results of measurements for a sample obtained by the sample measuring apparatus, the measurements including an initial measurement for the sample and a secondary measurement which is performed on the sample following the initial measurement;

a data management computer communicably connected to the first computer, wherein the data management computer includes a display section; an input device; and a controller which is programmed to:

cause the display section to display a first result screen which shows a result of the initial measurement for the sample, wherein the first result screen includes an object for receiving an instruction to display a second result screen which shows a result of the secondary measurement for the sample with the first result screen;

receive the instruction by use of the input device while displaying the first result screen; and cause the display section to display, in a response to the instruction, the second result screen, wherein when the measurement result of the sample received from the measuring apparatus satisfies a predetermined condition, the controller automatically transmits to the measuring apparatus an instruction to carry out the secondary measurement.

24. A sample analyzing system according to claim 23, wherein the predetermined condition is whether error occurs or not in the measurement results of the sample.

25. A computer program product for causing a computer including an input device and a display section to function as a data management computer for a sample measuring apparatus, the computer program product comprising:

a computer readable medium; and instruction code stored in the computer readable medium for causing the computer to perform acts comprising:

causing the display section to display a first result screen which shows a result of an initial measurement for the sample, wherein the first result screen includes an object for receiving an instruction to display a second result screen which shows a result of the secondary measurement for the sample with the first result screen receiving the instruction to display the second result screen via an input device while displaying the first result screen; and causing the display section to display, in a response to the instruction, the second result, wherein when the measurement result of the sample received from the measuring apparatus satisfies a predetermined condition, automatically transmitting to the sample measuring apparatus an instruction to carry out the secondary measurement.

26. A computer program product according to claim 25, wherein the predetermined condition is whether error occurs or not in the measurement results of the sample.

* * * * *